(12) United States Patent
Marczyk et al.

(10) Patent No.: US 11,666,328 B2
(45) Date of Patent: *Jun. 6, 2023

(54) RETRACTION MECHANISM WITH CLUTCH-LESS DRIVE FOR USE WITH SURGICAL APPARATUS

(71) Applicant: Covidien LP, Mansfield, MA (US)

(72) Inventors: Stanislaw Marczyk, Stratford, CT (US); Joseph Bender-Zanoni, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,484

(22) Filed: Mar. 1, 2022

(65) Prior Publication Data
US 2022/0175373 A1  Jun. 9, 2022

Related U.S. Application Data

(60) Continuation of application No. 16/751,336, filed on Jan. 24, 2020, now Pat. No. 11,259,800, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 2017/00398* (2013.01);
(Continued)

(58) Field of Classification Search
CPC .... A61B 17/07207; A61B 2017/00398; A61B 2017/2923
See application file for complete search history.

(56) References Cited

U.S. PATENT DOCUMENTS 1,877,162 A * 9/1932 Day ................. B25C 1/06
227/137
4,508,523 A 4/1985 Leu
(Continued)

FOREIGN PATENT DOCUMENTS

EP 1520521 A1 4/2005
EP 1813203 A2 8/2007
(Continued)

OTHER PUBLICATIONS

European Search Report for EP 09251693 dated Nov. 5, 2009 (3 pages).

*Primary Examiner* — Andrew M Tecco
(74) *Attorney, Agent, or Firm* — Carter, DeLuca & Farrell LLP

(57) ABSTRACT

A retraction mechanism allows the full distal retraction of the firing drive from various positions. The retraction mechanism has been developed for use with a hand held surgical apparatus. An embodiment of the retraction mechanism includes a drive member, a first pulley, a second pulley, and a firing drive. The drive mechanism is configured to be driven by a motor. The first pulley is configured to rotate when the motor drives the drive mechanism. The second pulley is movable relative to the first pulley between a proximal position and a distal position. The firing drive is movable relative to the first pulley between proximal and distal positions. In operation, the first pulley rotates in a first direction in response to a distal translation of the firing drive and wherein the firing drive moves proximally upon rotation of the first pulley in a second direction.

20 Claims, 20 Drawing Sheets

Related U.S. Application Data continuation of application No. 15/233,180, filed on Aug. 10, 2016, now Pat. No. 10,575,846, which is a continuation of application No. 14/032,369, filed on Sep. 20, 2013, now Pat. No. 9,433,415, which is a division of application No. 13/198,016, filed on Aug. 4, 2011, now Pat. No. 8,556,152, which is a division of application No. 12/486,122, filed on Jun. 17, 2009, now Pat. No. 8,011,551.

(60) Provisional application No. 61/077,197, filed on Jul. 1, 2008.

(51) Int. Cl.
*A61B 17/00* (2006.01)
*A61B 17/29* (2006.01)

(52) U.S. Cl.
CPC ............... *A61B 2017/2923* (2013.01); *A61B 2017/2943* (2013.01)

(56) References Cited

U.S. PATENT DOCUMENTS

| | | |
|---|---|---|
| 4,544,090 A | 10/1985 | Warman et al. |
| 5,143,453 A | 9/1992 | Weynant nee Girones |
| 5,207,697 A | 5/1993 | Carusillo et al. |
| 5,223,663 A | 6/1993 | Bender-Zanoni et al. |
| 5,350,355 A | 9/1994 | Sklar |
| 5,383,880 A | 1/1995 | Hooven |
| 5,467,911 A * | 11/1995 | Tsuruta ............... A61B 17/0684 227/19 |
| 5,482,100 A | 1/1996 | Kuhar |
| 5,518,163 A | 5/1996 | Hooven |
| 5,518,164 A | 5/1996 | Hooven |
| 5,667,517 A | 9/1997 | Hooven |
| 5,897,562 A | 4/1999 | Bolanos et al. |
| 5,980,548 A | 11/1999 | Evans et al. |
| 6,017,354 A | 1/2000 | Culp et al. |
| 6,085,368 A * | 7/2000 | Robert ............... A61G 7/1051 74/400 |
| 6,090,123 A | 7/2000 | Culp et al. |
| 6,126,651 A | 10/2000 | Mayer |
| 6,231,565 B1 | 5/2001 | Tovey et al. |
| 6,264,086 B1 | 7/2001 | McGuckin, Jr. |
| 6,264,087 B1 | 7/2001 | Whitman |
| 6,295,330 B1 | 9/2001 | Skog et al. |
| 6,315,184 B1 | 11/2001 | Whitman |
| 6,329,778 B1 | 12/2001 | Culp et al. |
| 6,443,973 B1 | 9/2002 | Whitman |
| 6,505,768 B2 | 1/2003 | Whitman |
| 6,520,971 B1 * | 2/2003 | Perry ............... A61B 17/2909 606/139 |
| 6,533,157 B1 | 3/2003 | Whitman |
| 6,698,643 B2 | 3/2004 | Whitman |
| 6,716,233 B1 | 4/2004 | Whitman |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,979,328 B2 | 12/2005 | Baerveldt et al. |
| 6,981,941 B2 | 1/2006 | Whitman et al. |
| 7,000,819 B2 | 2/2006 | Swayze et al. |
| 7,032,798 B2 | 4/2006 | Whitman et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,128,254 B2 | 10/2006 | Shelton, IV et al. |
| 7,143,926 B2 | 12/2006 | Shelton, IV et al. |
| 7,364,061 B2 | 4/2008 | Swayze et al. |
| 7,422,136 B1 | 9/2008 | Marczyk |
| 7,431,188 B1 * | 10/2008 | Marczyk ............... A61B 17/105 606/139 |
| 7,464,846 B2 | 12/2008 | Shelton, IV et al. |
| 7,510,107 B2 | 3/2009 | Timm et al. |
| 7,648,055 B2 * | 1/2010 | Marczyk ............... A61B 17/0643 606/139 |
| 7,833,018 B2 | 11/2010 | Alexander |
| 7,963,433 B2 * | 6/2011 | Whitman ............... A61B 17/072 227/19 |
| 8,006,887 B2 * | 8/2011 | Marczyk ............... A61B 17/0644 606/139 |
| 8,011,551 B2 | 9/2011 | Marczyk et al. |
| 8,092,493 B2 * | 1/2012 | Marczyk ............... A61B 17/1155 606/139 |
| 8,240,537 B2 * | 8/2012 | Marczyk ............... A61B 17/135 227/176.1 |
| 8,272,554 B2 * | 9/2012 | Whitman ............... A61B 17/072 227/19 |
| 8,342,379 B2 * | 1/2013 | Whitman ............... A61B 90/98 227/19 |
| 8,479,967 B2 | 7/2013 | Marczyk |
| 8,556,152 B2 | 10/2013 | Marczyk et al. |
| 2002/0025891 A1 | 2/2002 | Colosky et al. |
| 2002/0165541 A1 | 11/2002 | Whitman |
| 2003/0073981 A1 | 4/2003 | Whitman et al. |
| 2004/0045561 A1 | 3/2004 | Alexander |
| 2004/0094597 A1 | 5/2004 | Whitman et al. |
| 2004/0232201 A1 | 11/2004 | Wenchell et al. |
| 2005/0067458 A1 | 3/2005 | Swayze et al. |
| 2005/0070958 A1 | 3/2005 | Swayze et al. |
| 2005/0131390 A1 | 6/2005 | Heinrich et al. |
| 2005/0178813 A1 | 8/2005 | Swayze et al. |
| 2005/0187576 A1 | 8/2005 | Whitman et al. |
| 2005/0192609 A1 | 9/2005 | Whitman et al. |
| 2005/0228341 A1 | 10/2005 | Edgerley |
| 2006/0151567 A1 | 7/2006 | Roy |
| 2006/0175375 A1 | 8/2006 | Shelton et al. |
| 2006/0212069 A1 | 9/2006 | Shelton |
| 2006/0273135 A1 | 12/2006 | Beetel |
| 2006/0278680 A1 * | 12/2006 | Viola ............... A61B 17/072 227/176.1 |
| 2007/0023476 A1 | 2/2007 | Whitman et al. |
| 2007/0023477 A1 | 2/2007 | Whitman et al. |
| 2007/0102473 A1 | 5/2007 | Shelton et al. |
| 2007/0175947 A1 | 8/2007 | Ortiz et al. |
| 2007/0175949 A1 | 8/2007 | Shelton et al. |
| 2007/0175951 A1 * | 8/2007 | Shelton, IV ...... A61B 17/07207 227/176.1 |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175962 A1 | 8/2007 | Shelton et al. |
| 2007/0175964 A1 | 8/2007 | Shelton et al. |
| 2008/0029570 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0164296 A1 | 7/2008 | Shelton et al. |
| 2008/0308604 A1 | 12/2008 | Timm et al. |
| 2011/0192883 A1 * | 8/2011 | Whitman ............... A61B 17/072 227/178.1 |
| 2013/0277409 A1 | 10/2013 | Marczyk |

FOREIGN PATENT DOCUMENTS

| | | |
|---|---|---|
| EP | 1813205 A1 | 8/2007 |
| EP | 1872727 A1 | 1/2008 |

(56) References Cited

FOREIGN PATENT DOCUMENTS

| | | | |
|---|---|---|---|
| EP | 1980214 | A2 | 10/2008 |
| WO | 9729694 | A1 | 8/1997 |
| WO | 2004032760 | A2 | 4/2004 |

* cited by examiner

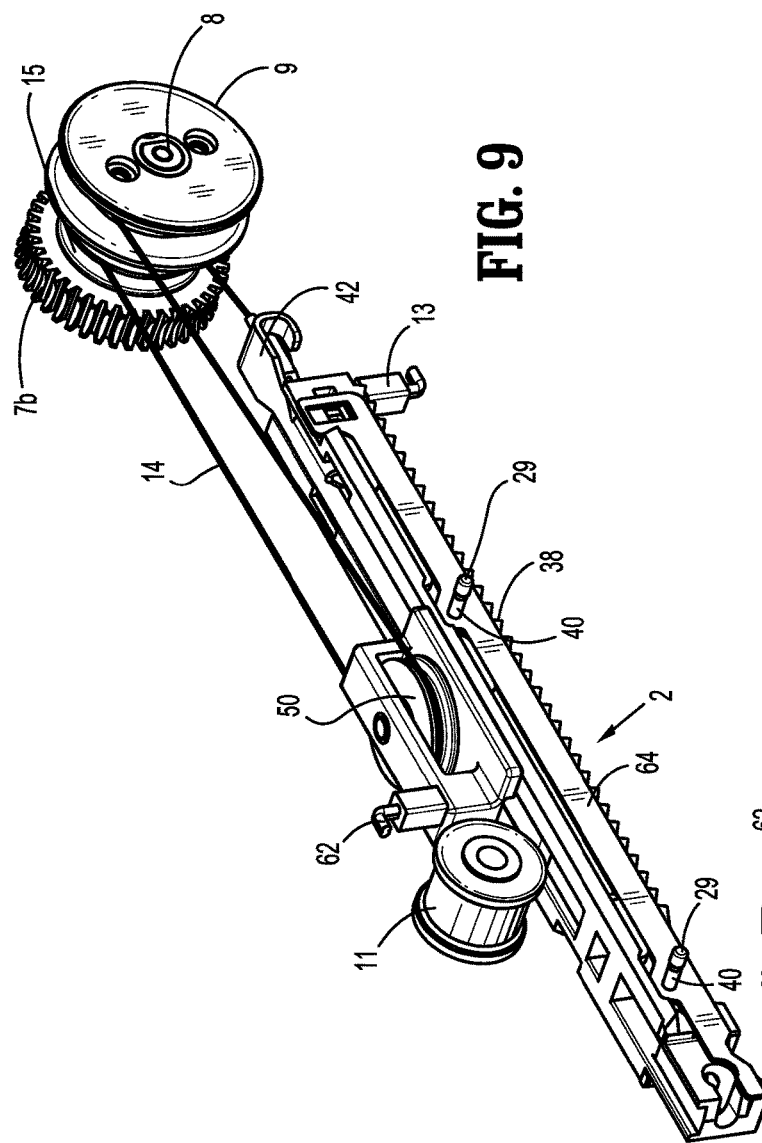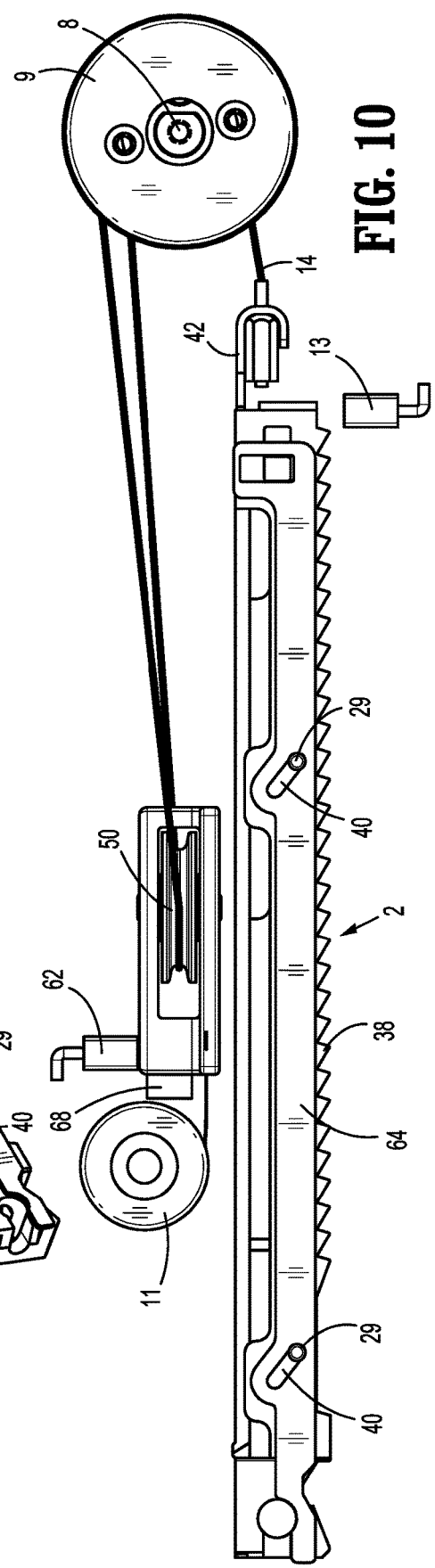

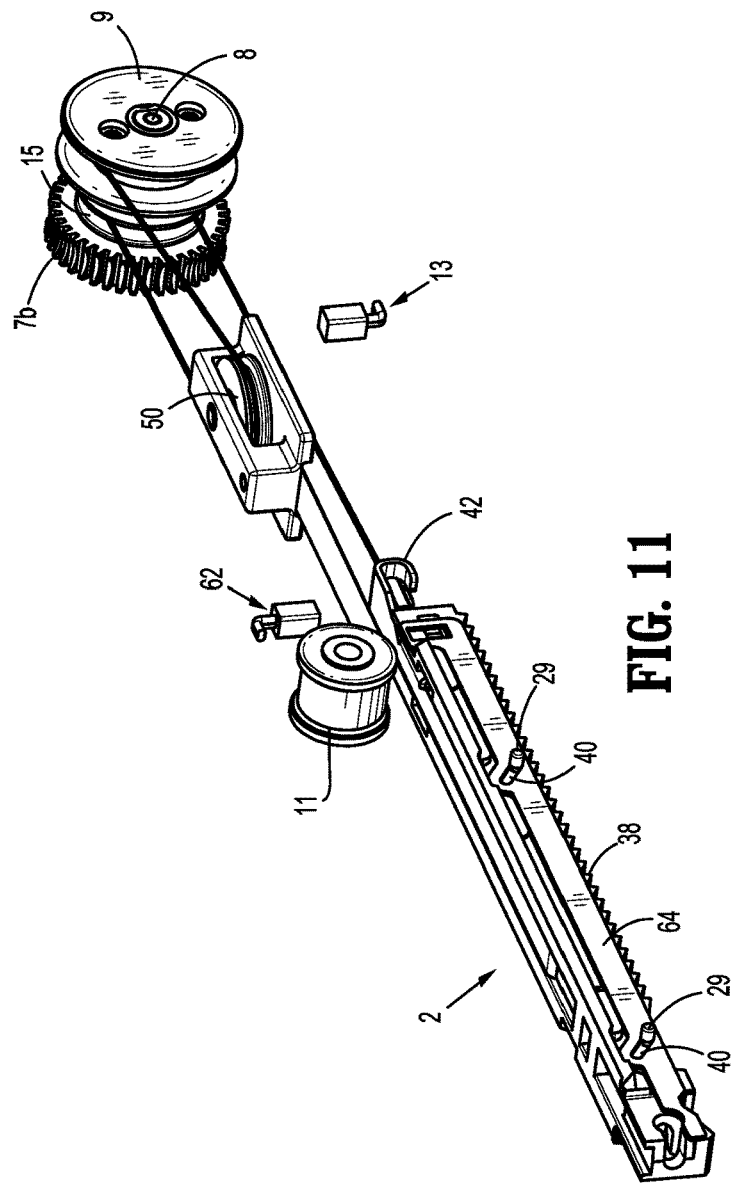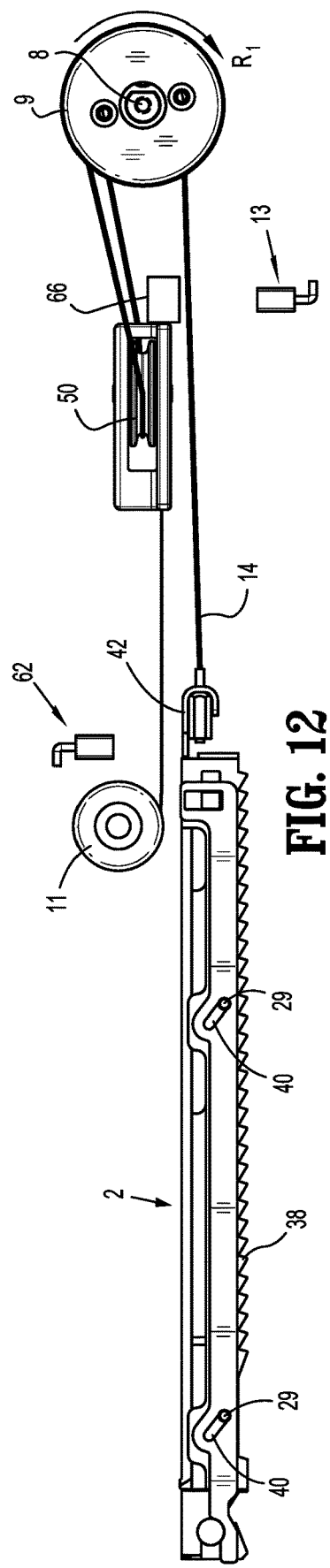

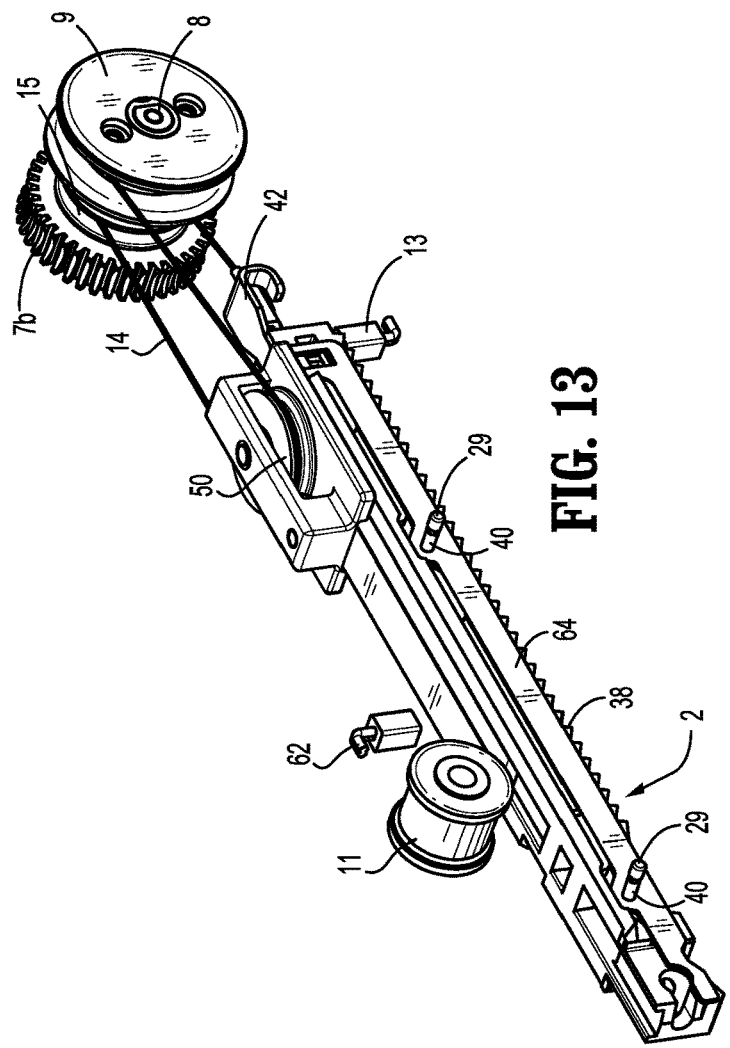
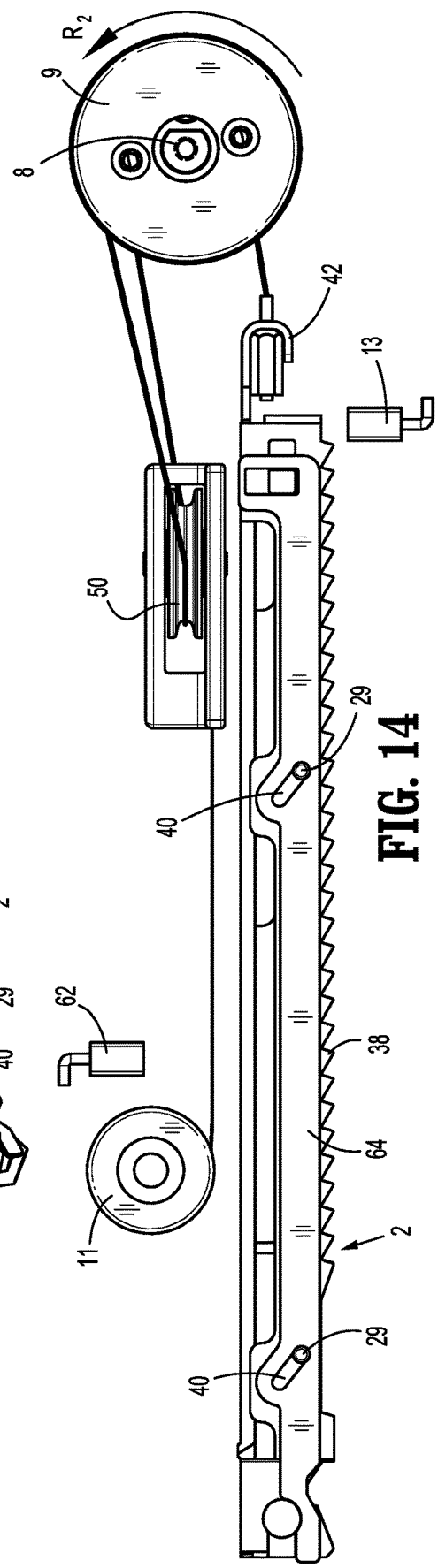

RETRACTION MECHANISM WITH CLUTCH-LESS DRIVE FOR USE WITH SURGICAL APPARATUS

CROSS-REFERENCE TO RELATED APPLICATIONS

The present application is a continuation of U.S. patent application Ser. No. 16/751,336, filed Jan. 24, 2020, which is a continuation of U.S. patent application Ser. No. 15/233,180, filed Aug. 10, 2016, now U.S. Pat. No. 10,575,846, which is a continuation of U.S. patent application Ser. No. 14/032,369, filed Sep. 20, 2013, now U.S. Pat. No. 9,433,415, which is a divisional of U.S. patent application Ser. No. 13/198,016, filed Aug. 4, 2011, now U.S. Pat. No. 8,556,152, which is a divisional of U.S. patent application Ser. No. 12/486,122 filed Jun. 17, 2009, now U.S. Pat. No. 8,011,551, which claims priority to, and the benefit of, U.S. Provisional Patent Application Ser. No. 61/077,197, filed on Jul. 1, 2008, the entire contents of each of these prior applications are hereby incorporated by reference.

BACKGROUND

The present disclosure relates to hand held surgical stapling apparatus. More particularly, the present disclosure relates to retraction mechanisms for use with hand held surgical stapling apparatus.

Surgical apparatus capable of fastening tissue layers are well known in the art. In general, surgical stapling apparatus include two elongated jaw members designed for capturing or clamping tissue. One jaw member typically contains a staple cartridge housing a plurality of staples. Conventional staple cartridges include at least two lateral rows of retention slots. These retention slots are adapted to receive staples. The other jaw member has an anvil that defines a surface for forming the staple legs as the staples are driven from the staple cartridge. The stapling operation is usually effected by cam members that translate through the staple cartridge. The cam members act on staple pushers to eject the staples from the staple cartridge. A knife may move axially between the rows of retention slots to cut or open the stapled tissue.

Another surgical stapling apparatus applies a double row of staples on each side of the incision. This surgical stapling apparatus has a disposable loading unit wherein a cam member moves through an elongate guide path between two sets of staggered staple carrying grooves. Staple drive members are located within the grooves and are positioned in such a manner so as to be contacted by the longitudinally moving cam member. The staple members eject the staples in the staple cartridge as the cam member moves axially along the elongate guide path.

Each of the apparatus described hereinabove is designed for use in conventional surgical procedures wherein surgeons have direct manual access to the operative site. In endoscopic or laparoscopic procedures, however, surgery is performed through a small incision or through a narrow cannula inserted through small entrance wound in the skin. Endoscopic surgical stapling devices have been developed to address the specific needs of endoscopic and laparoscopic surgical procedures. A few examples of endoscopic surgical stapling devices are disclosed in U.S. Pat. Nos. 5,312,023; 5,326,013; and 6,241,139, the entire contents of each of which are incorporated herein by reference.

Some of the instruments described in the patents listed above have retraction mechanisms to return the firing drive of the instrument to a retracted or proximal position. These retraction mechanisms include a pair of retractor knobs movably positioned along a barrel portion of a handle assembly. The retraction knobs can be manually pulled proximally to retract the firing drive to its original position after firing the instrument.

Other endoscopic stapling instruments include powered retraction mechanisms. For instance, U.S. Patent Application Publication No. 2008/0245842, filed Apr. 9, 2007, now U.S. Pat. No. 800,685, the entire contents of which is hereby incorporated by reference, discloses a surgical stapling apparatus including a powered retraction mechanism. An embodiment of this retraction mechanism includes a motor operatively associated with a pulley and a slip clutch. The pulley is configured to retract the firing drive of the surgical stapling apparatus once the slip clutch moves to its engaged position.

The surgical apparatus described above have provided significant clinical benefits. Nonetheless, improvements to these instruments are possible. For instance, it would be beneficial to provide a surgical stapling apparatus with a clutch-less powered retraction mechanism to reduce the weight and size of the mechanism. By minimizing the number of parts, the retraction mechanism could be easily placed within a handle assembly of a surgical stapling apparatus.

SUMMARY

The present disclosure relates to a retraction mechanism for use with a hand held surgical apparatus. An embodiment of the retraction mechanism includes a drive member, a first pulley, a second pulley, and a firing drive. The drive mechanism is configured to be driven by a motor. The first pulley is operatively associated with the drive mechanism and is configured to rotate when the motor drives the drive mechanism. The second pulley is disposed in mechanical cooperation with the first pulley and is movable relative to the first pulley between a proximal position and a distal position. The firing drive is operatively coupled to the first pulley and the second pulley and is movable relative to the first pulley between proximal and distal positions. In operation, the first pulley rotates in a first direction in response to a distal translation of the firing drive. Moreover, the firing drive moves proximally upon rotation of the first pulley in a second direction.

In an alternative embodiment, the retraction mechanism includes a motor, a speed reducing mechanism, a rotatable shaft, a retraction pulley, a shuttle pulley, and a firing drive. The speed reducing mechanism is configured to be driven by a motor. The rotatable shaft is operatively associated with the speed reducing mechanism. The retraction pulley is configured to rotate upon rotation of the shaft. During use, a first rotation of the retraction pulley in a first direction moves the firing drive of a surgical apparatus proximally. The shuttle pulley is distally biased and is movable between proximal and distal positions. A distal translation of the firing drive is possible because the shuttle pulley can move to a proximal position. A rotation of the retraction pulley in a direction counter to said first direction moves the shuttle pulley in the distal direction.

In another embodiment, the retraction mechanism includes a first shaft, a worm positioned around the first shaft and a worm gear operatively coupled to the worm. The worm is configured to rotate concomitantly with the first shaft and to move relative to the first shaft between a proximal position and a distal position. The worm gear is operatively coupled to the worm and configured to rotate upon rotation of the worm. Rotating the worm gear in a first direction moves a firing drive of a surgical apparatus proximally.

In a further embodiment, the retraction mechanism includes a first shaft configured to rotate about an axis, a pulley configured to rotate, a first post operatively coupled to the first shaft, a second post operatively connected to the pulley, and an engagement member attached to the first post. In operation, rotating the pulley in a first direction moves a firing drive of a surgical apparatus proximally. The first post is configured to rotate upon rotation of the first shaft. The second post is configured to rotate concomitantly with the pulley. The engagement member is configured engage the second post. The second post is configured to rotate concomitantly with the first post when the engagement member engages the second post.

BRIEF DESCRIPTION OF THE DRAWINGS

Various embodiments of the presently disclosed surgical stapling apparatus and retraction mechanisms are described herein with reference to the drawings:

FIG. 9 is a perspective view of the retraction mechanism of FIG. 8 with the firing drive in a proximal position and a shuttle pulley in a distal position;

FIG. 10 is a side view of the retraction mechanism of FIG. 8 with the firing drive in the proximal position and a shuttle pulley in the distal position;

FIG. 11 is a perspective view of the retraction mechanism of FIG. 8 with the firing drive in the distal position and the shuttle pulley in a proximal position;

FIG. 12 is a side view of the retraction mechanism of FIG. 8 with the firing drive in the distal position and the shuttle pulley in the proximal position;

FIG. 13 is a perspective view of the retraction mechanism of FIG. 8 with the firing drive in the proximal position and the shuttle pulley in the proximal position;

FIG. 14 is a side view of the retraction mechanism of FIG. 8 with the firing drive in the proximal position and the shuttle pulley in the proximal position;

DETAILED DESCRIPTION OF THE DRAWINGS

Figure 1:
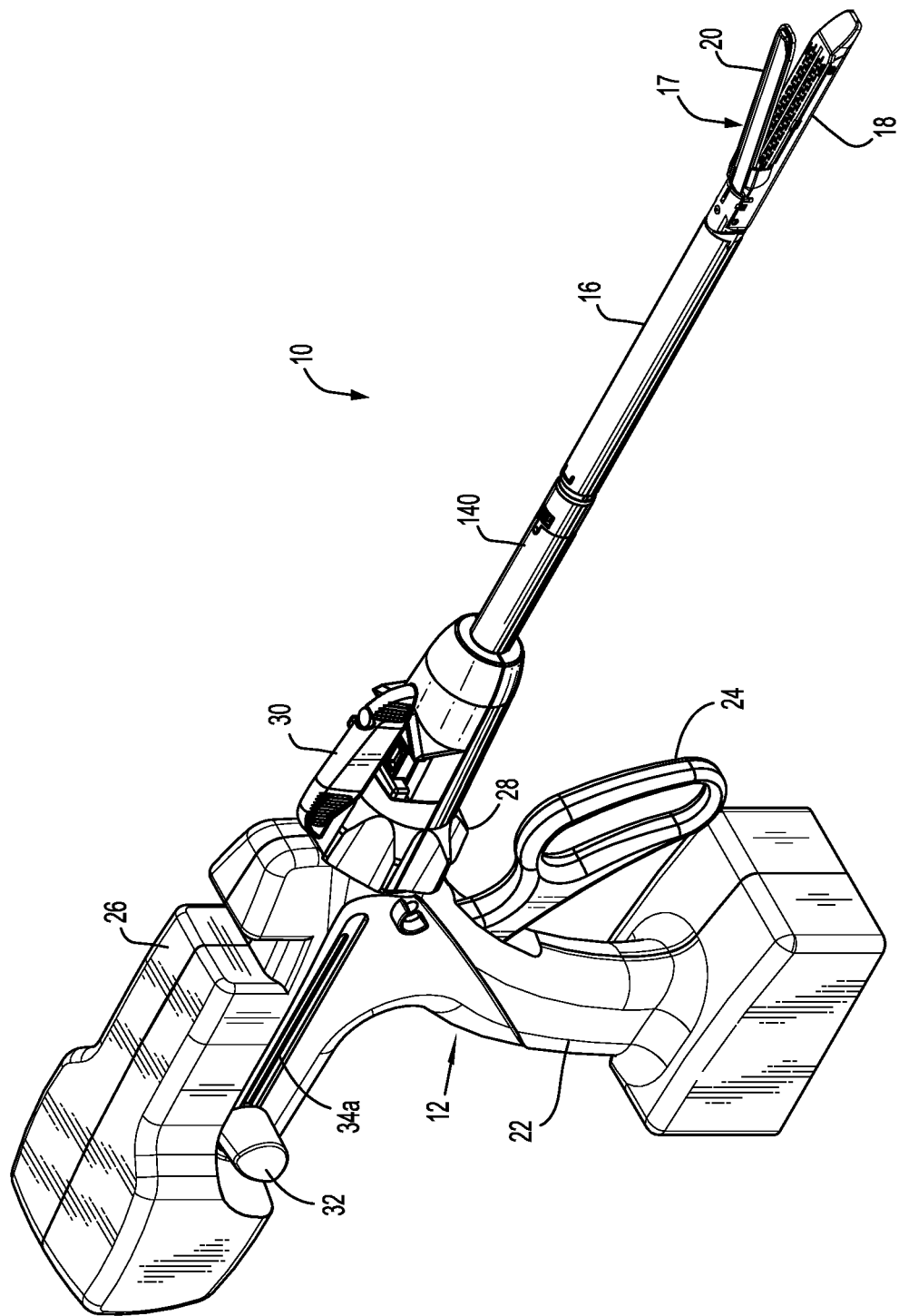
FIG. 1 is a perspective view of a surgical stapling apparatus according to an embodiment of the present disclosure.

Embodiments of the presently disclosed surgical stapling apparatus will now be described in detail with reference to the drawings in which like reference numerals designate identical or corresponding elements in each of the several views. In the drawings and the description that follows, the term "proximal," as is traditional, will refer to the end of the surgical stapling apparatus, or component thereof, that is closest to the operator, while the term "distal" will refer to the end of the apparatus, or component thereof, that is farthest from the operator. Singular forms, such as "a," "an," and "the," include the plural form. Likewise, plural forms include the singular forms, unless clearly stated otherwise.

Figure 2:
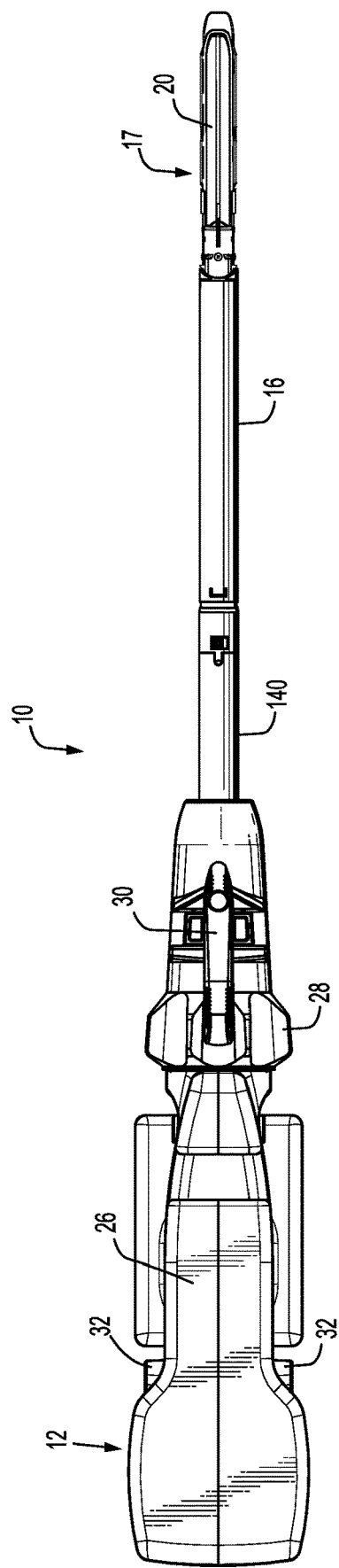
FIG. 2 is a top view of the surgical stapling apparatus of FIG. 1.
Figure 3:
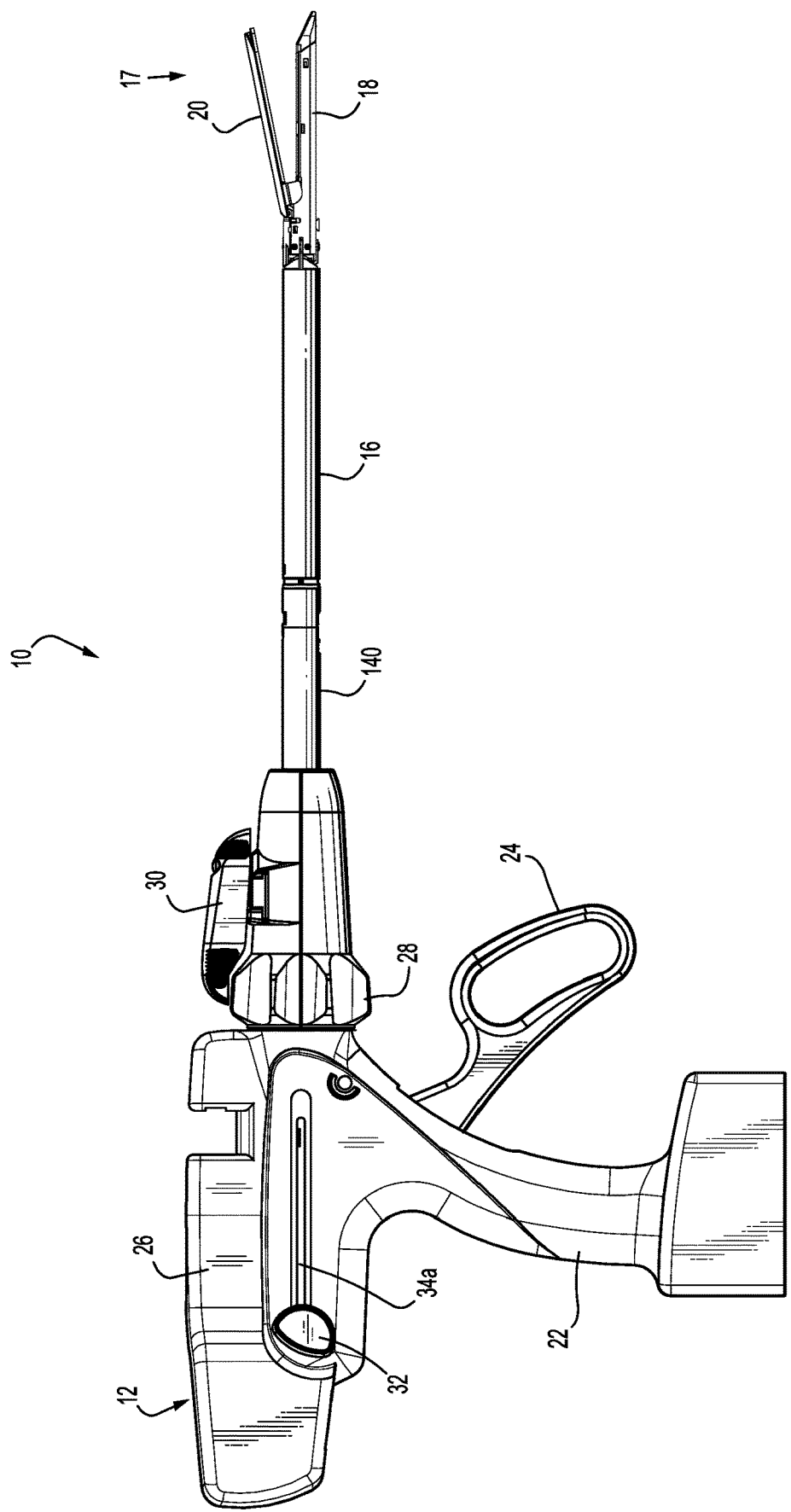
FIG. 3 is a side view of the surgical stapling apparatus of FIG. 1.

FIGS. 1-3 illustrate an embodiment of the presently disclosed surgical stapling apparatus shown generally as 10. In the interest of brevity, this disclosure will primarily focus on systems, methods and structures for returning a firing drive of surgical stapling apparatus 10 to its retracted or proximal position after firing. U.S. Pat. No. 6,953,139, the entire contents of which are incorporated herein by reference, contains a detailed discussion of the structure and operation of surgical stapling apparatus 10.

Briefly, surgical stapling apparatus 10 is an endoscopic instrument including a handle assembly 12 and an elongated body 140 extending therefrom. A single use loading unit ("SULU") 16 is releasably secured to a distal end of elongated body 140. Although the drawings show SULU 16, one skilled in the art will recognize that any other suitable tool or end effector can be releasably secured to elongated body 140. In the embodiment depicted in FIG. 1, SULU 16 includes a tool assembly 17 having a cartridge assembly 18 and an anvil assembly 20. Cartridge assembly 18 houses a plurality of surgical staples. Anvil assembly 20, in turn, is movably secured in relation to cartridge assembly 18. Due to its structural configuration, anvil assembly 20 is capable of moving between an open position spaced from cartridge assembly 18 and an approximated or clamped position in juxtaposed alignment with cartridge assembly 18. In alternative arrangements, the anvil assembly 20 is stationary and the cartridge assembly 18 is movable.

Altogether, SULU 16 is configured to apply at least one row of staples. SULUs 16 may have various staple line lengths and configurations. In some embodiments, for instance, SULUs 16 have staple line lengths measuring from about 30 mm to about 60 mm in length. In addition to staple line length, other features of SULU 16 may adjust to the different needs depending on the circumstances. SULU 16, for example, may include a tool assembly 17 pivotable about its proximal end, as disclosed in U.S. Pat. No. 6,953,139, the entire contents of which are hereby incorporated by reference. In this embodiment, a user controls the pivotable movement of tool assembly 17 through an articulation lever 30 positioned on handle assembly 12.

Figure 4:
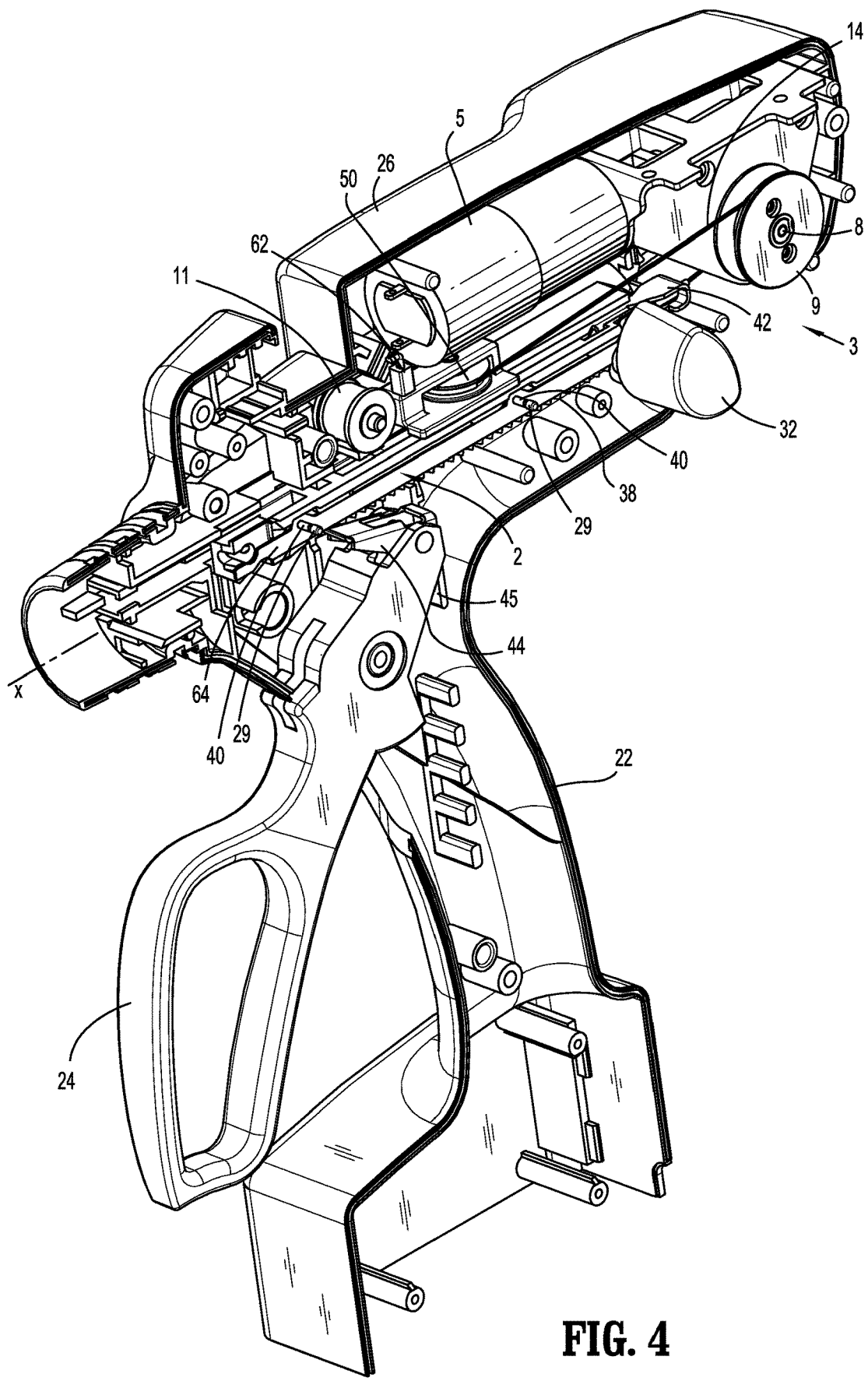
FIG. 4 is a perspective cutaway view of a handle assembly of the surgical stapling apparatus of FIG. 1, showing a firing drive.

In addition to controlling the pivoting motion of tool assembly 17, handle assembly 12 directs the actuation of tool assembly 17. To this end, handle assembly 12 includes a stationary handle member 22, a movable handle member 24, and a barrel portion 26 defining a longitudinal axis "X," as shown in FIG. 4. Barrel portion 26 has a rotatable member 28 mounted on a distal end thereof. In use, rotatable member 28 facilitates rotation of elongated body 140 with respect to handle assembly 12. As discussed above, handle assembly 12 additionally includes articulation lever 30 disposed on the distal end of barrel portion 26 adjacent to rotatable member 28. Articulation lever 30 facilitates articulation of tool assembly 17.

Figure 5:
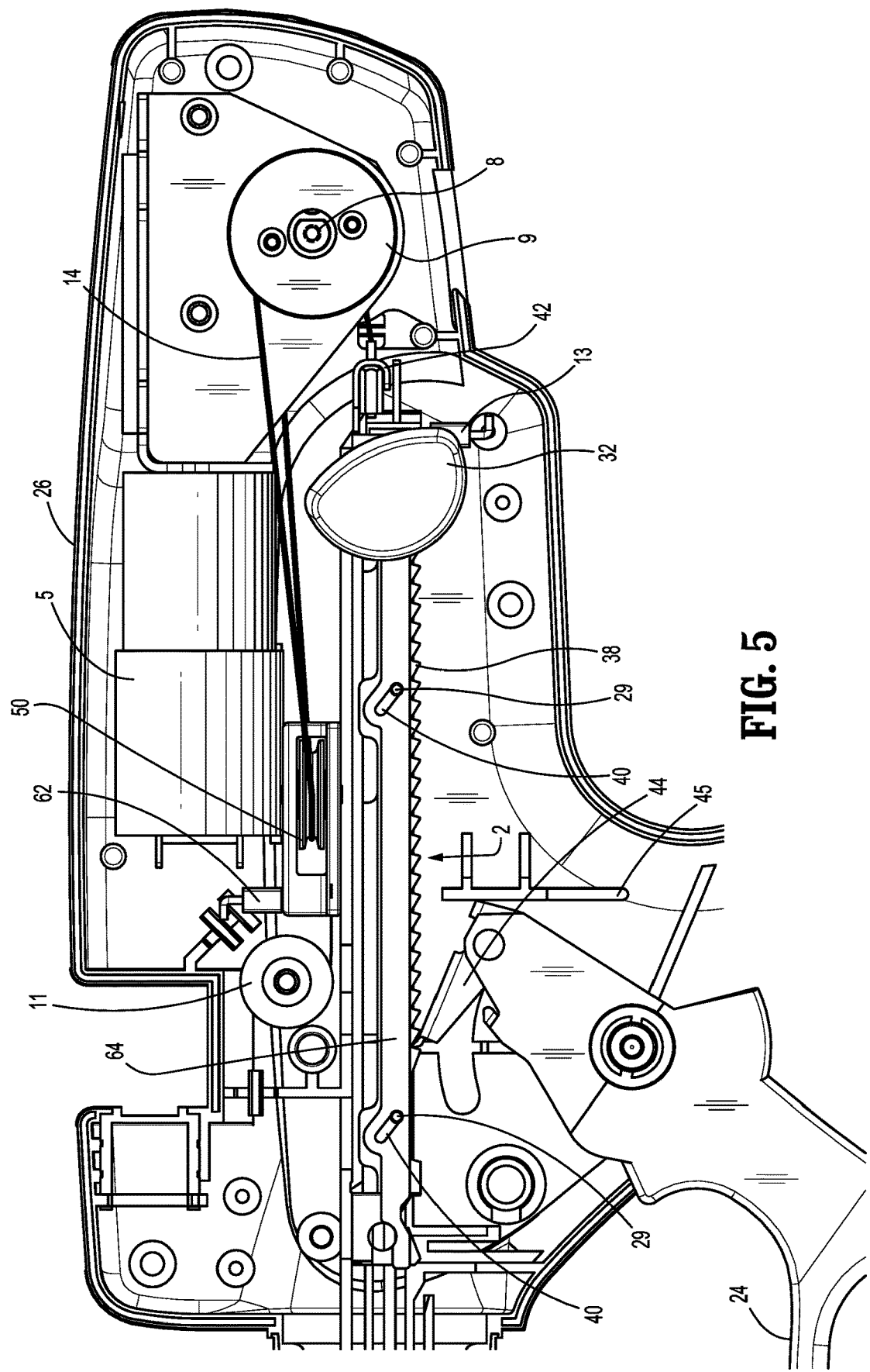
FIG. 5 is a side cutaway view of a portion of the handle assembly of FIG. 4, showing a retraction pulley.
Figure 6:
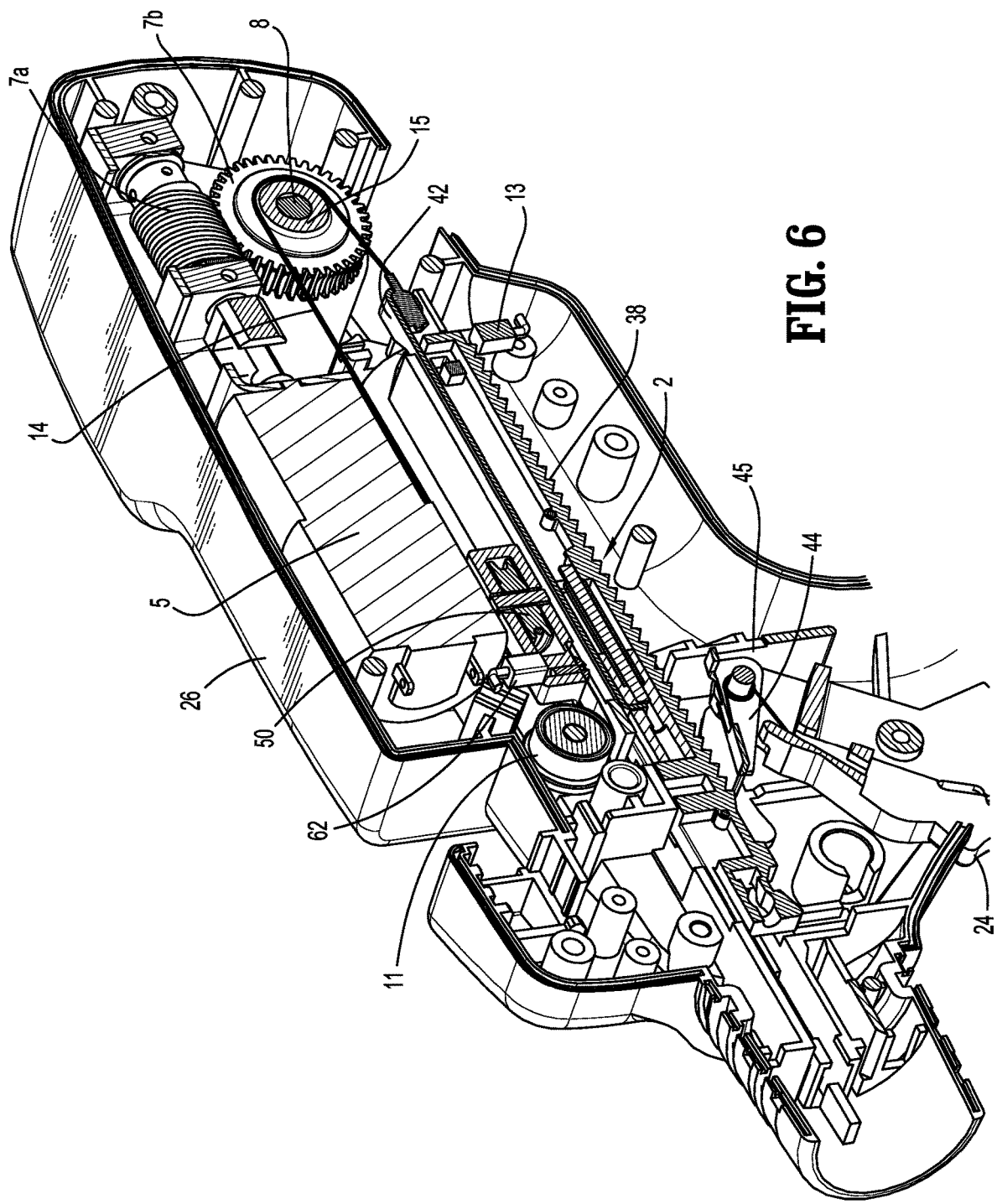
FIG. 6 is a perspective cutaway view of a portion of the handle assembly of FIG. 4.

With reference to FIGS. 4-6, barrel portion 26 encompasses a firing drive 2 including a toothed rack 38. A pawl 44 is mounted to selectively engage toothed rack 38 and advance firing drive 2 in a distal direction in response to manipulation of movable handle member 24 (see FIG. 1) through an actuating stroke. The mounting portion of pawl 44 is adapted to interact with an abutment wall 45. During operation, pawl 44 is rotated out of engagement with toothed rack 38 when reaching abutment wall 45.

To fire apparatus 10, a user can move movable handle member 24 toward a stationary handle member 22 (FIG. 4). Thereupon, pawl 44 engages toothed rack 38 and drives firing drive 2 distally. The distal advancement of firing drive 2 caused by one full stroke of movable handle member 24 will be dictated by the size and configuration of firing drive 2. Firing drive 2 may have various sizes and configurations.

In some embodiments, to complete the staple firing operation, movable handle member 24 is once again approximated toward stationary handle 22, causing pawl 44 to engage toothed rack 38 and advance firing drive 2 in a distal direction another 15 mm. Thus, in these embodiments, two complete strokes of actuation handle 24 advances firing drive 2 thirty (30) mm within barrel portion 26, causing the sequential ejection of all the surgical staples in cartridge assembly 18 (FIG. 1). If desired, the operator may incrementally advance firing drive 2 by multiple short strokes, wherein the minimum advancement is dictated by the linear distance between the teeth on rack 38. Therefore, while two complete strokes of a stroke distance of 15 mm may be used (to fire a 30 mm disposable loading unit), complete strokes are not necessary or required. Surgical stapling apparatus 10 may be configured to have various stroke distances, for example 45 or 60 mm.

Figure 8:
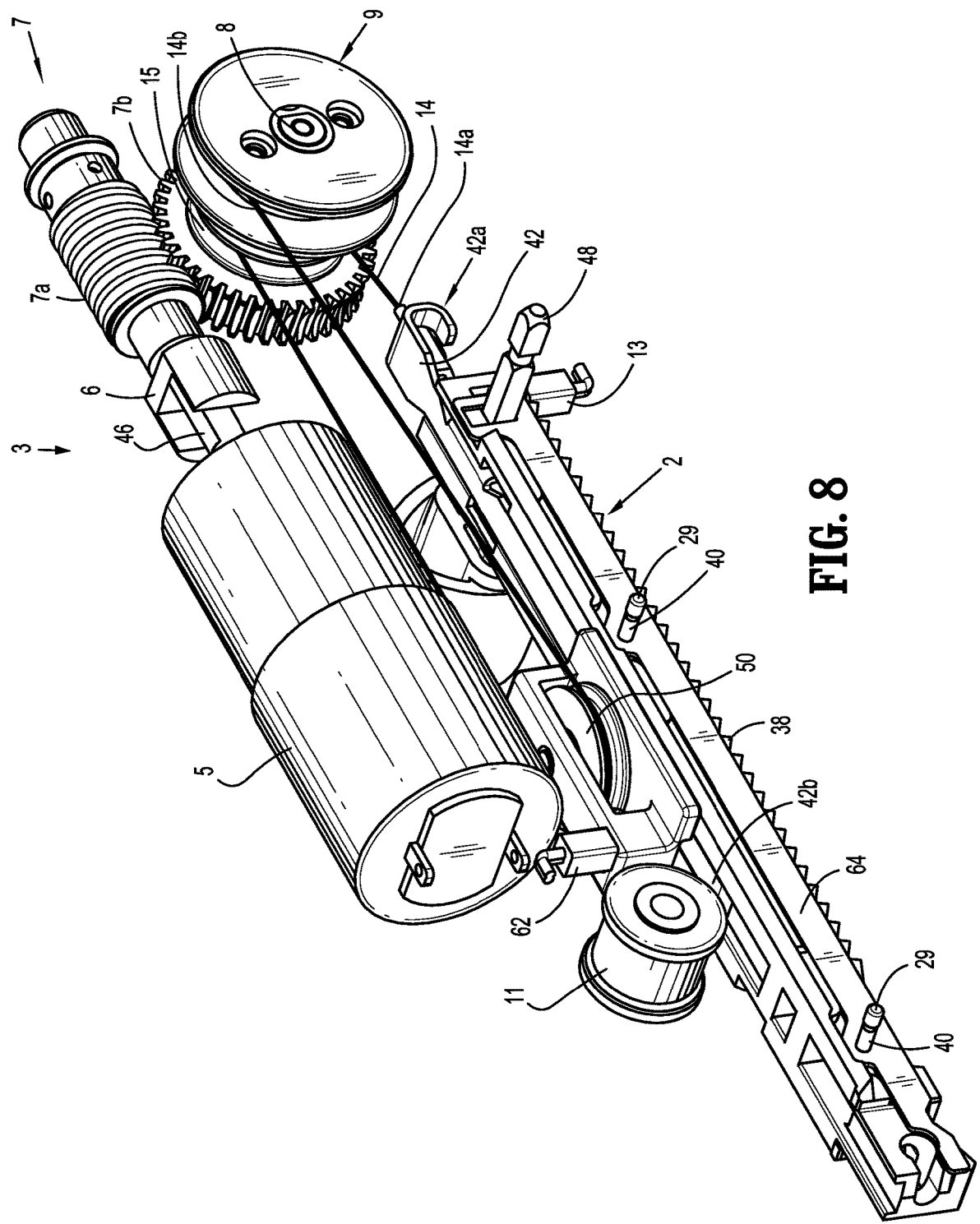
FIG. 8 is a perspective view of an embodiment of a retraction mechanism operatively associated with the firing drive of the surgical stapling apparatus of FIG. 1.

With continued reference to FIGS. 4-6, a pair of retractor knobs 32 is connected to a proximal end of firing drive 2 through a coupling pin 48 (see FIG. 8). Retractor knobs 32 are movably positioned along barrel portion 26. Specifically, at least a portion of coupling pin 48 is dimensioned and configured to translate within a pair of longitudinal slots 34a formed on handle assembly 12, as seen in FIG. 1. A release plate 64 is operatively associated with firing drive 2 and is mounted for movement with respect thereto in response to manipulation of retractor knobs 32. A pair of spaced apart pins 29 extends outwardly from a lateral face of firing drive 2 to engage a pair of corresponding angled cam slots 40 formed in release plate 64. U.S. Pat. No. 7,044,353, the entire contents of which is hereby incorporated by reference, describes in detail the structure and manual operation of the firing drive 2 and release plate 64. In brief, a user manually translates retractor knobs 32 in a proximal direction to retract firing drive 2 to its original or proximal position.

To enable retraction, firing drive 2 includes a distally biased connector 42 having proximal and distal ends 42a, 42b, as shown in FIG. 8. Connector 42 is mounted on a top portion of firing drive 2. A flexible member 14 interconnects connecter 42 and a first or retraction pulley 9. The present disclosure envisions that flexible member 14 may be a cable, a chain, a wire, or any other suitable apparatus capable of interconnecting connector 42 and retraction pulley 9. As shown in FIG. 8, a first end 14a of flexible member 14 is attached to the proximal end 42a of connector 42, while a second end 14b of flexible member 14 is attached to retraction pulley 9 of retraction mechanism 3.

Figure 7:
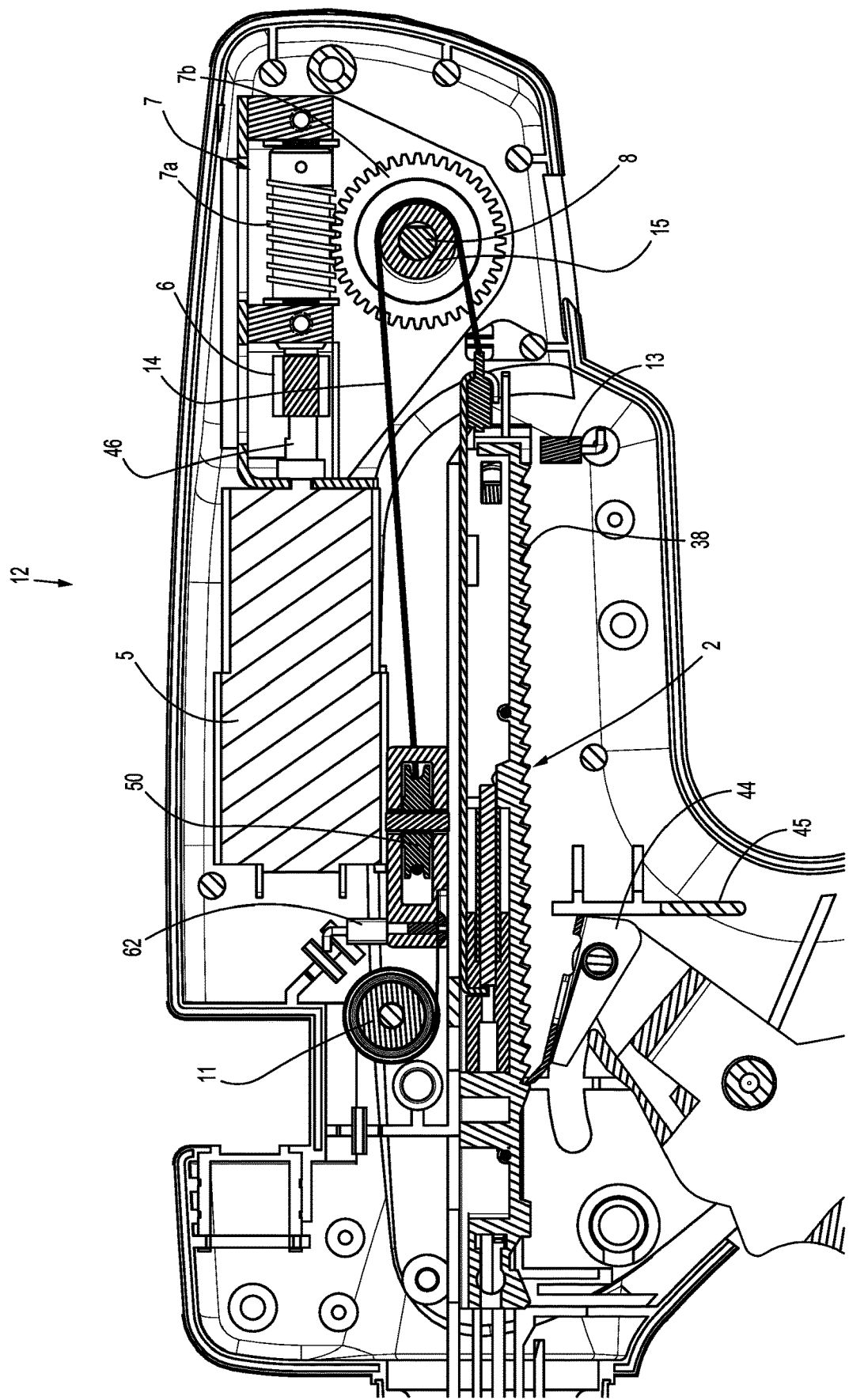
FIG. 7 is a side cutaway view of the handle assembly of FIG. 4, showing a speed reducing mechanism.

Referring to FIGS. 7 and 8, retraction mechanism 3 is generally positioned in parallel with longitudinal axis "X" (FIG. 4) within handle assembly 12 and facilitates retraction of firing drive 2 to proximal position. (See FIG. 4). To this end, retraction mechanism 3 is operatively associated with firing drive 2 through flexible member 14. In addition, retraction mechanism 3 includes a motor 5 (often including a speed reducing gearhead) disposed in electro-mechanical cooperation with a speed reducing mechanism or transmission 7. In some embodiments, motor 5 is electrically linked to a controller, such as a microprocessor, which can control motor travel, speed, and direction of rotation based on the inputs from sensor and/or activation switches. Particularly, a transmission shaft 46 is mounted to motor 5. A coupling 6 interconnects transmission shaft 46 and speed reducing mechanism or drive mechanism 7. In the depicted embodiment, speed reducing mechanism 7 effectively reduces the rotational motion supplied by motor 5. In certain embodiments, speed reducing mechanism 7 includes a first gear 7a configured to mesh with a second gear 7b. In the embodiment shown in FIGS. 7 and 8, first gear 7a constitutes a worm and second gear 7b is a worm gear. It is contemplated that first gear 7a and second gear 7b may be other kinds of gears such as bevel or helical gears. First gear 7a is secured to coupling 6 and, in operation, rotates in response to a rotation of transmission shaft 46. Second gear 7b is rotatably connected to a shaft 8. Thus, shaft 8 is adapted to rotate upon rotation of second gear 7b.

Retraction pulley 9 is operatively connected to shaft 8 and flexible member 14, as discussed hereinabove. During use, the rotation of shaft 8 causes the rotation of pulley 9. In addition to pulley 9, a third or idler pulley 15 is mounted to shaft 8 and disposed between second gear 7b and pulley 9. Flexible member 14 connects firing drive 2 to retraction pulley 9 through idler pulley 15 and a second or shuttle pulley 50. A spring 11 biases shuttle pulley 50 in a distal direction up to a distal stop 68. (See FIG. 10). Distal stop 68 is secured to an inner surface of handle assembly 12. Shuttle pulley 50, albeit distally biased, is adapted to move between proximal and distal positions. A proximal stop 66, however, limits the proximal movement of shuttle pulley 50. (See FIG. 12). Shuttle pulley 50 can move proximally up to proximal stop 66. Proximal stop 66 is attached to an inner surface of handle assembly 12.

Retraction mechanism 3 includes at least one sensor to monitor the movement of shuttle pulley 50. In the depicted embodiment, retraction mechanism 3 has a first sensor 62 disposed on a distal position and configured to determine whether the shuttle pulley 50 has reached its distal position. Similarly, a second sensor 13 is located on a proximal positioned and designed to determine whether firing drive 2 has reached the proximal position.

Referring to FIGS. 9-14, a user initially operates tool assembly 17 (FIG. 1) by actuating movable handle member 24 (FIG. 1) to clamp and fasten tissue portions. Before actuating tool assembly 17 (FIG. 1), firing drive 2 is disposed in a proximal position while shuttle pulley 50 is located in a distal position, as seen in FIGS. 9 and 10. Spring 11 biases shuttle pulley 50 distally all the way to distal stop 68 (FIG. 10). Additionally, motor 5 should be turned off before and during the actuation of tool assembly 17 (FIG. 1). During this time, motor 5 locks retraction pulley 9. As the user actuates movable handle member 24 (FIG. 1), firing drive 2 moves axially until it reaches a distal position, as illustrated in FIGS. 11 and 12. Since firing drive 2 and shuttle pulley 9 are operatively connected to each other through flexible member 14, the distal motion of firing drive 2 translates shuttle pulley 50 towards a proximal position, as shown in FIGS. 11 and 12. The proximal position of firing drive 2 depends on the length of the stroke of handle member 24 (FIG. 1) required for a given cartridge length. Throughout this process, spring 11 maintains flexible member 14 in tension to prevent, or at least inhibit, entanglement.

After firing surgical staples, the surgeon activates motor 5 by, for instance, pressing a button (not shown). Motor 5 drives speed reducing mechanism 7, causing a rotation of retraction pulley 9 in a first direction R1, as shown in FIG. 12. The rotation of retraction pulley 9 in the first direction R1 causes the axial proximal motion of firing drive 2 to the fully proximal position (see FIG. 14). While retraction pulley 9 rotates in the first direction R1, shuttle pulley 50 maintains its proximal position due to the resistance of proximal stop 66 and acts as a stationary pulley to allow the motion of flexible member 14 to retract firing drive 2. Once firing drive 2 reaches the fully proximal position (FIG. 14), second sensor 13 sends a signal to a controller. The controller stops motor 5 and thereafter activates motor 5 again. This time, however, motor 5 rotates transmission shaft 46 rapidly in an opposite direction. This rotation of transmission shaft 46 causes the rotation of retraction pulley 9 in a second direction R2 (FIG. 14). The rotation of retraction pulley 9 in the second direction R2 releases flexible member 14 and allows spring 11 to move shuttle pulley 50 to its distal position, as illustrated in FIGS. 9 and 10. When first sensor 62 detects the presence of shuttle pulley 50 in the distal position, sensor 62 sends a signal to motor 5. When motor 5 receives the signal from sensor 62, motor 5 stops. At this time, surgical stapling apparatus 10 is ready for the next cycle. If firing drive 2 is retracted manually through retraction knobs 32, spring 11 eliminates the slack of flexible member 14 by moving shuttle pulley 50 to its distal position (FIG. 9) without the need to activate motor 5.

Figure 15:
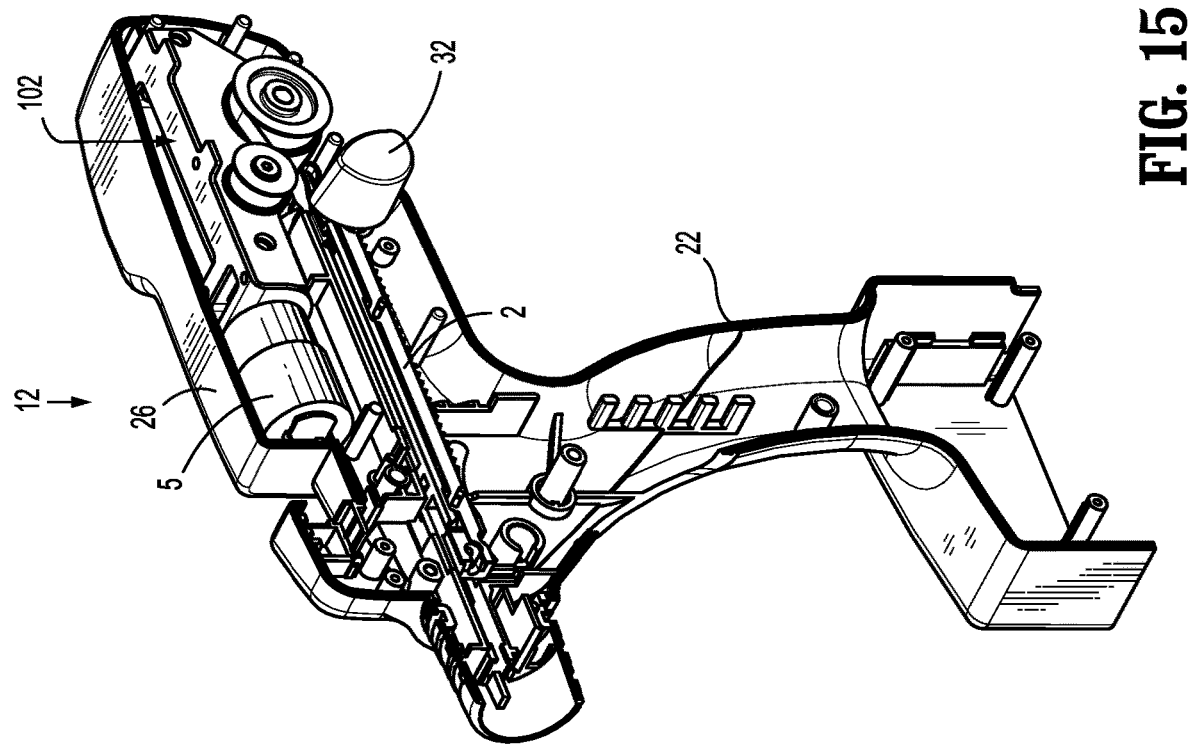
FIG. 15 is a perspective cutaway view of the handle assembly of the surgical stapling apparatus of FIG. 1 showing another embodiment of a retraction mechanism.

With reference to FIG. 15, handle assembly 12 may include an alternative retraction mechanism 102. Retraction mechanism 102 is operatively coupled to firing drive 2 and is configured to urge firing drive 2 from a distal position to a proximal "home" position after firing surgical stapling apparatus 10 (FIG. 1). During operation, an operator may manually or mechanically retract firing drive 2 via retraction mechanism 102. To facilitate manual retraction, retraction mechanism 102 includes at least one retraction knob 32 connected to a proximal end of firing drive 2, as discussed above. (See also FIG. 4). Retractor knobs 32 are movably positioned along barrel portion 26 of handle assembly 12. An operator can move firing drive 2 from a distal position to a proximal "home" position by pulling retraction knobs 32 in proximal direction after firing surgical stapling apparatus 10 (FIG. 1). The positions of the knobs 32 indicate the position of firing drive 2 during clamping, firing, and retraction. Alternatively, the operator can retract firing drive 2 after firing surgical stapling apparatus 10 (FIG. 1) by activating electrical motor 5. As discussed above, electrical motor 5 may include an integrated gearbox (not shown) and powers retraction mechanism 102 during operation.

With reference to FIGS. 16-19, retraction mechanism 102 includes a frame 113 supporting the internal components of retraction mechanism 102. Motor 5 is operatively connected to a shaft 111 through a coupling 106. Although the drawings show a specific coupling 106, any suitable coupling or connection means may interconnect motor 5 and shaft 111. Shaft 111 is coupled to a worm 107 of a drive or speed reducing mechanism 130 and includes longitudinal keys 132 extending along its length. Longitudinal keys 132 engage slots (not shown) extending along an inner surface of worm 107 and preclude, or at least hinder, rotation of worm 107 relative to shaft 111. Thus, shaft 111 rotates in unison with worm 107. Worm 107 surrounds at least a portion of shaft 111 and can move relative to shaft 111 between a proximal position W2 and a distal position W1. In fact, the engagement between longitudinal keys 132 of shaft 111 and the slots (not shown) of worm 107 facilitates movement of worm 107 along shaft 111. Retraction mechanism 102 further includes a pair of bearings 112a, 112b located at each end of shaft 111. First bearing 112a is mounted on a distal end of shaft 111, while second bearing 112b is mounted on a proximal end of shaft 111. Each bearing 112a, 112b can support a radial load as well as an axial load. Worm 107 is engaged to worm gear 108. Accordingly, worm gear 108 rotates upon rotation of worm 107. In particular, worm 107 includes a thread 134 formed thereabout. Worm gear 108 also includes a plurality of teeth 136 disposed around its circumference. Teeth 136 of worm gear 108 are configured to mesh with thread 134 of worm 107.

Worm 107 and worm gear 108 collectively form speed reducing mechanism 130. In the depicted embodiment, speed reducing mechanism 130 constitutes a worm drive mechanism. It is envisioned, however, that any suitable apparatus, means, or parts, may make up speed reducing mechanism 130. In operation, speed reducing mechanism 130 reduces the rotation speed of motor 5, while increasing torque.

Figure 17:
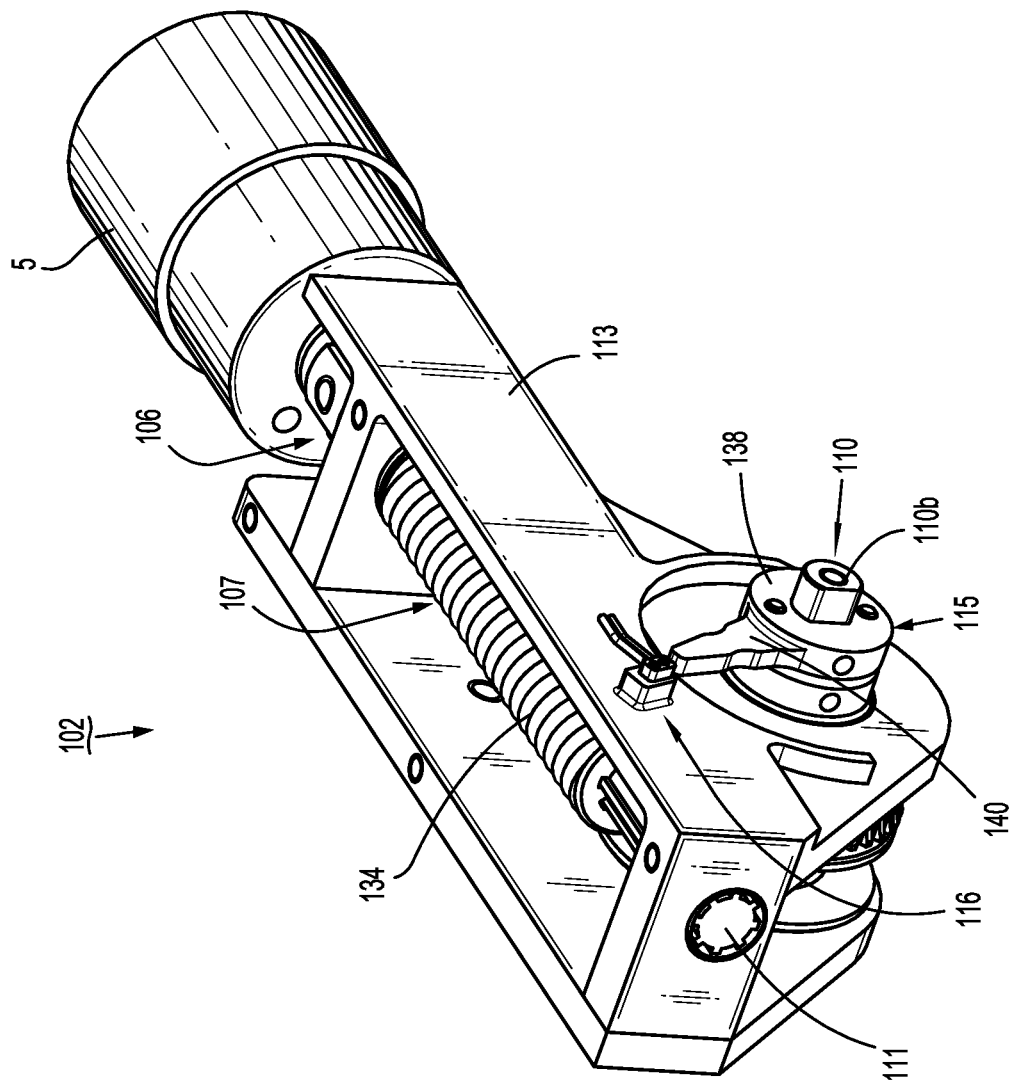
FIG. 17 is a rear perspective view of the retraction mechanism of FIG. 15, showing a frame supporting certain components of the retraction mechanism.
Figure 18:
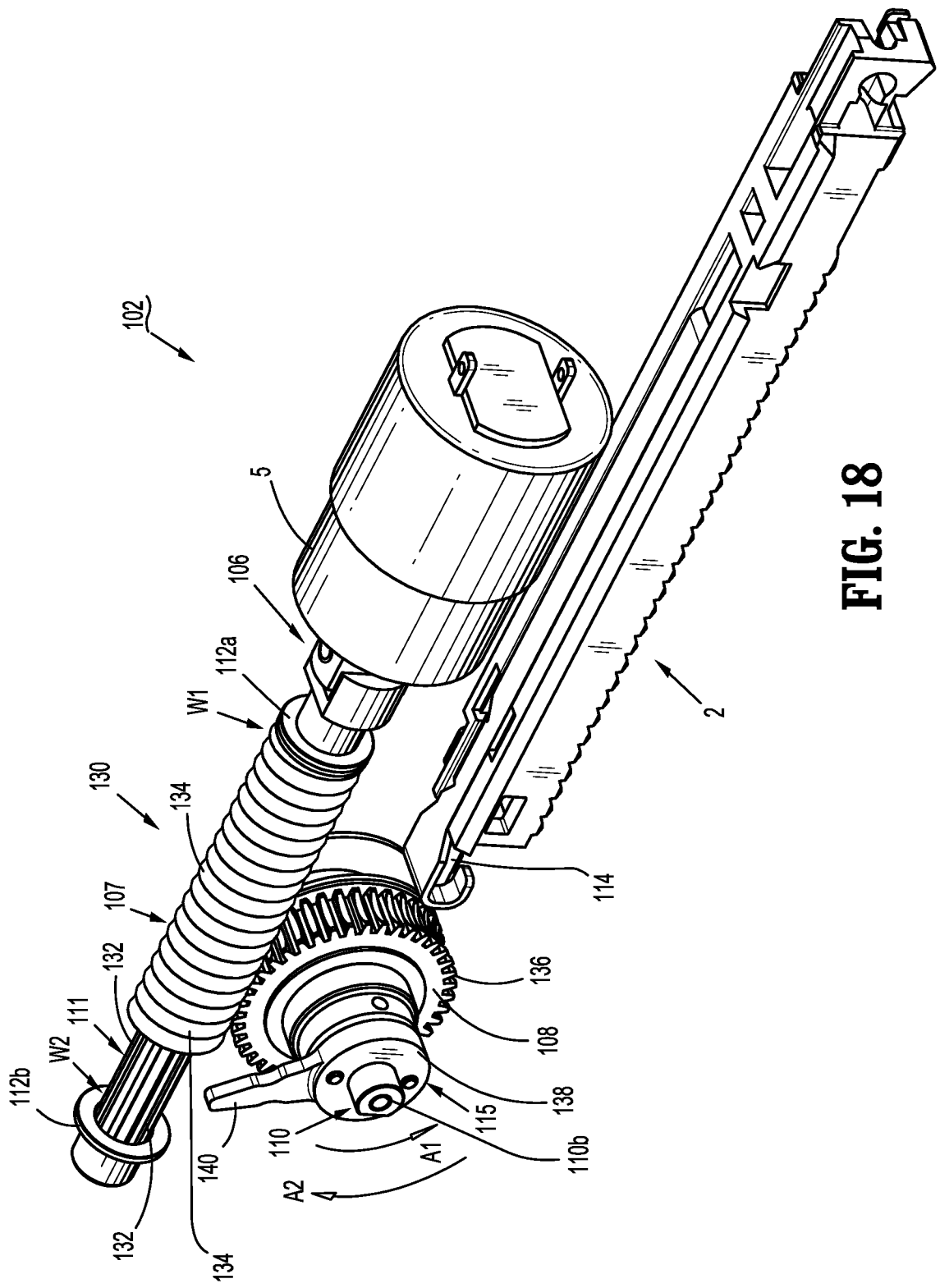
FIG. 18 is front perspective view of the retraction mechanism of FIG. 15 without the frame and showing a post.
Figure 19:
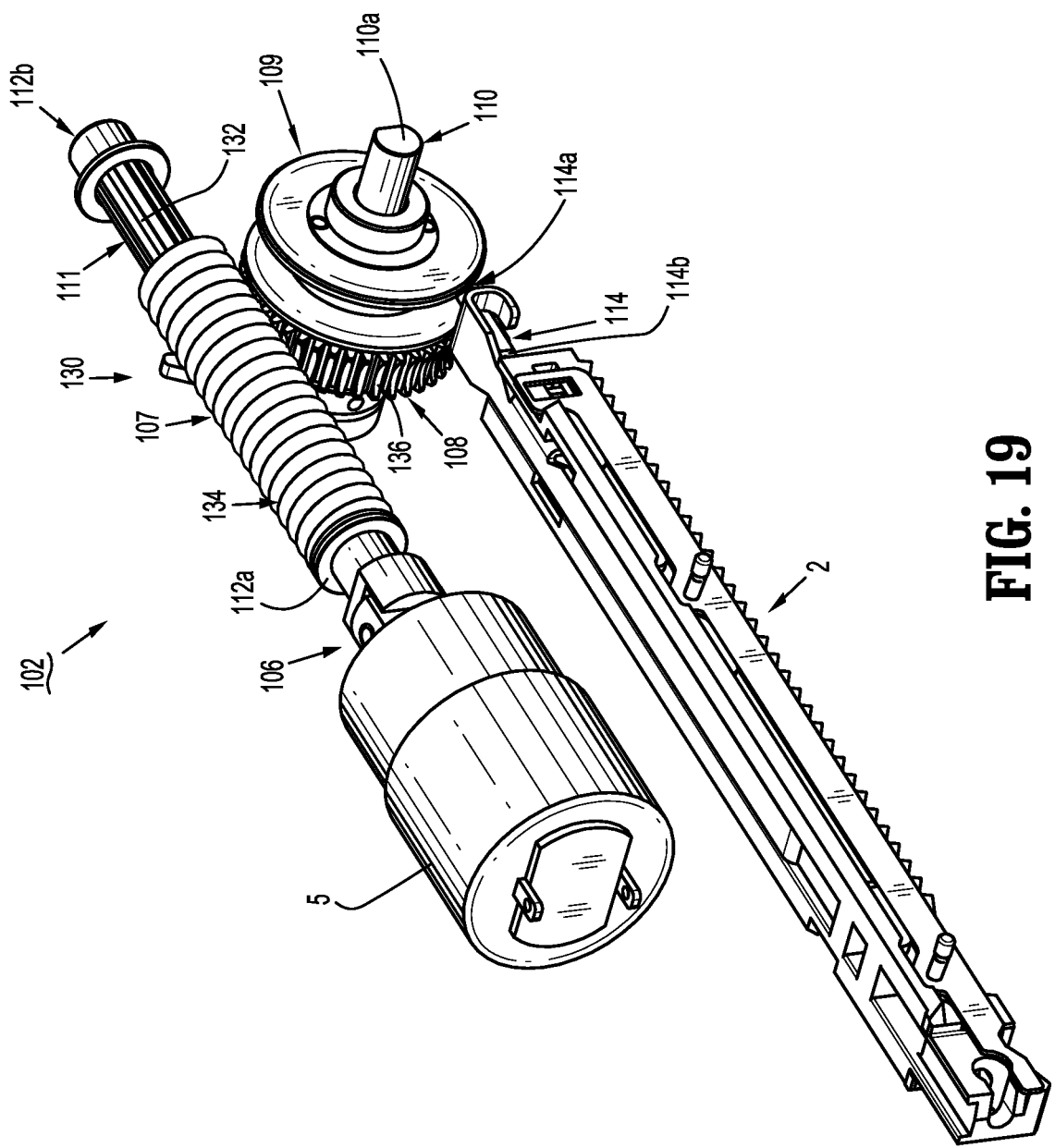
FIG. 19 is a front perspective view of the retraction mechanism of FIG. 15 without a frame and showing a pulley.

In the embodiment shown in FIGS. FIGS. 16-19, worm gear 108 is rotatably coupled to a pulley 109 (FIG. 19). Consequently, pulley 109 rotates upon rotation of worm gear 108. Pulley 109 and worm gear 108 are both mounted on a shaft 110. Shaft 110 is oriented substantially orthogonal or transversely relative to shaft 111. A flexible member 114, such as a cable, a chain, a wire, or any other suitable flexible element, interconnects pulley 109 and flexible drive 2. As seen in FIG. 19, a first end 114a of flexible member 114 is attached to pulley 109, whereas a second end 114b of flexible member 114 is attached to firing drive 2.

Shaft 110 has a first end 110a (FIG. 19) and a second end 110b (FIG. 18). A post 115 is mounted on second end 110b of and includes an annular section 138 and an arm 140 extending radially from annular section 138. Annular section 138 of post 115 surrounds second end 110b of shaft 110. Due to this arrangement, post 115 rotates in response to a rotation of shaft 110. Arm 140 of post 115 is configured to activate a sensor or switch 116 (FIG. 17). Element 116 may be a conventional electrical switch or a sensor such as a position sensor. It is contemplated that sensor 116 may be a potentiometer, a Hall sensor, a piezo-electric transducer, an inductive position sensor, or any other sensor suitable to detect the position of arm 140 of post 115. As seen in FIG. 17, sensor or switch 116 is secured to an outer wall of frame 113.

Figure 16:
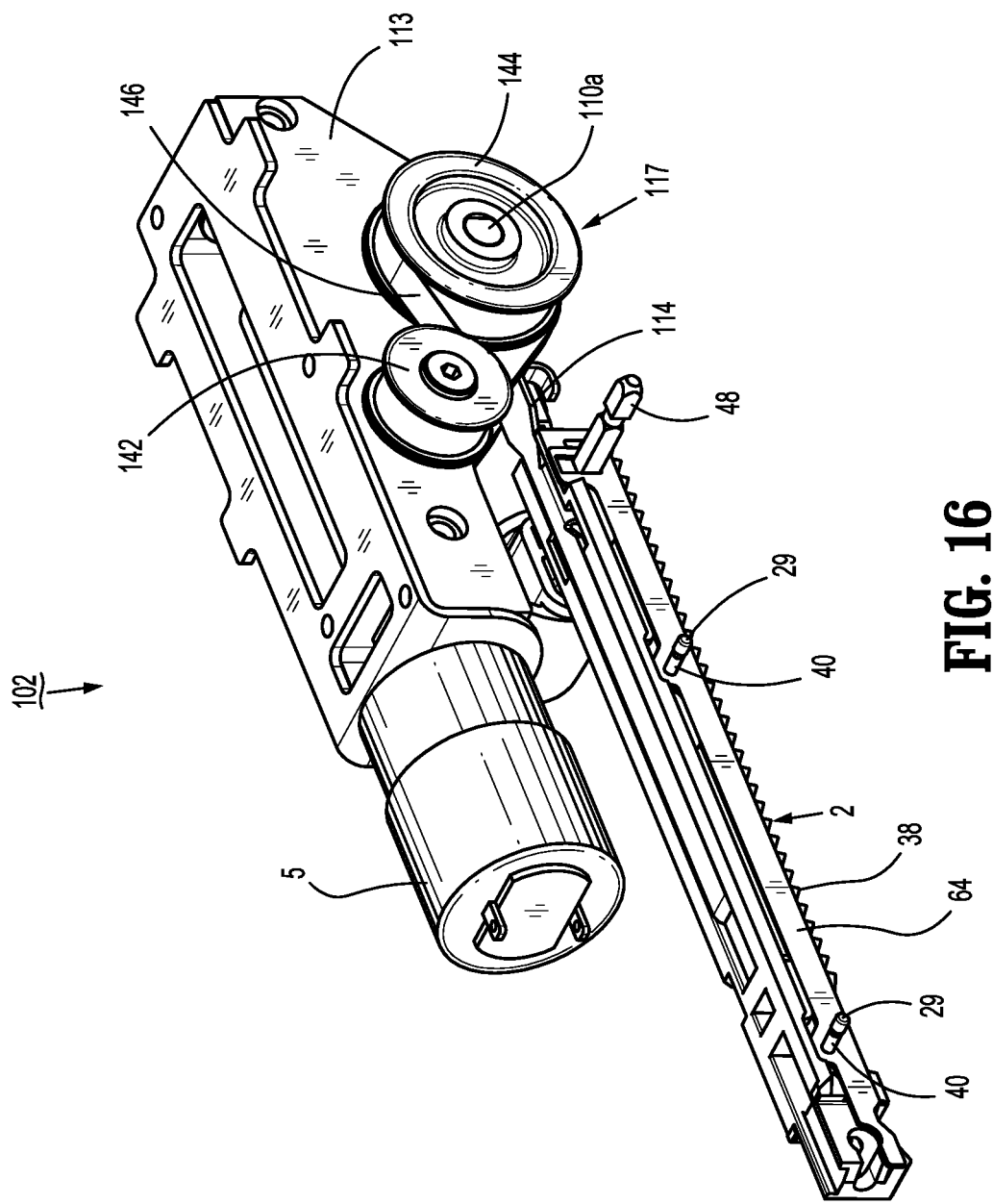
FIG. 16 is a front perspective view of the retraction mechanism of FIG. 15 operatively associated with the firing drive of the surgical stapling apparatus of FIG. 1.

As shown in FIG. 16, a spring motor 117 is operatively connected to first end 110a of shaft 110. In operation, spring motor 117 maintains flexible member 114 in tension and prevents, or at least inhibits, its entanglement. Spring motor 117 includes a storage drum 142 attached to an outer wall of frame 113, an output drum 144 mounted for rotation on first end 110a of shaft 110, and basing member 146, such as a spring, interconnecting storage drum 142 and output drum 144.

In operation, retraction mechanism 102 facilitates movement of firing drive 2 from a distal position to a proximal "home" position. In its initial state, firing drive 2 is located at a proximal "home" position and worm 107 is located in a distal "home" position W1 (FIG. 18). Motor 5 is turned off and, due to friction in its gearbox, motor 5 locks shaft 111. Upon actuation of handle assembly 12 (FIG. 15), firing drive 2 advances distally and pulls flexible member 114 in a distal direction. As flexible member 114 moves distally, pulley 109 rotates in a first direction A1 (FIG. 18) and drives worm gear 108. As a result, worm gear 108 also rotates in the first direction A1. While worm gear 108 rotates in the first direction A1, teeth 136 of worm gear 108 engage thread 134 of worm 107, causing the rotation of worm 107. Since shaft 111 is locked, worm 107 moves from a distal position W1 to a proximal position W2 (FIG. 18) in response to the rotation of worm gear 108. At this juncture, worm 107 and worm gear 108 acts as a rack and pinion.

At the end of firing, firing drive 2 is located in its distal position and worm 107 is located in its proximal position W2 (FIG. 18). The lengths of shaft 111 and worm 107 may vary. Therefore, in different embodiments, worm 107 may move different distances along shaft 111, thus permitting firing SULU 16 (FIG. 1) of various lengths.

After completing firing of surgical stapling apparatus 10 (FIG. 1), the operator presses a retraction switch (not shown) to activate motor 5. Motor 5 then rotates shaft 111. Shaft 111, in turn, drives and rotates worm 107. Since worm gear 108 resists rotation, worm 107 advances from proximal position W2 to distal position W1 with a screw motion. When worm 107 reaches bearing 112a, worm 107 can only rotate. At this point, worm 107 begins to drive worm gear 108 and pulley 109 in a second direction A2 (FIG. 18). Consequently, pulley 109 winds at least a portion of flexible member 114, dragging firing drive 2 to its proximal "home" position. As pulley 109 rotates in the second direction A2, post 115 rotates in the second direction A2 as well. Once firing drive 2 has reached its proximal "home" position, post 115 activates sensor or switch 116, which shuts off motor 5. Specifically, when arm 140 of post 115 is aligned with sensor or switch 116, sensor or switch 116 sends a signal to motor 5. Upon receiving this signal, motor 5 shuts off.

Alternatively, the operator may manually move firing drive 2 form a distal position to its proximal "home" position through retraction knobs 32 (FIG. 1). After firing surgical stapling apparatus 10, flexible member 114 slacks, allowing firing drive 2 to move from a proximal "home" position to a distal position. To move firing drive 2 back to its proximal "home" position, the operator moves retraction knobs 32 proximally along handle assembly 12. Due to the slack in flexible member 114, spring motor 117 rotates pulley 109 and worm gear 108 in the second direction A2 (FIG. 18). During this rotation, pulley 109 winds at least part of the slacking portions of flexible member 114, thereby tightening flexible member 114. In the meantime, the rotation of worm gear 108 causes worm 107 to move from proximal position W2 to distal position W1 along the now stationary shaft 111. At the end of the retraction, post 115 activates sensor or switch 116 and worm 107 reaches distal position W1 (FIG. 18). At this juncture, surgical stapling apparatus 10 (FIG. 1) is again ready for firing. In some embodiments, retraction mechanism 102 includes an additional sensor that monitors whether worm 107 has reached its proximal "home" position W1.

FIGS. 20-23 show another embodiment of a retraction mechanism 202 for incorporation into surgical stapling apparatus 10 (FIG. 1). Retraction mechanism 202, however, may be incorporated into any other suitable surgical instrument. In operation, retraction mechanism 202 mechanically moves firing drive 2 from a distal position to a proximal "home" position after firing surgical stapling apparatus 10 (FIG. 1).

As seen in FIGS. 20-23, retraction mechanism 202 includes a frame 213 for supporting the internal components of retraction mechanism 202 and is operatively coupled to motor 5. Motor 5 may include an integrated gearbox and can rotate a shaft 211 of retraction mechanism 202 through a coupling 206. Shaft 211 is securely coupled a worm 207. Worm 207 surrounds at least a portion of shaft 211. During operation, worm 207 and shaft 211 rotate concomitantly upon activation of motor 5. Worm 207 is engaged to a worm gear 208.

Worm 207 includes a thread 234 form thereabout and worm gear 208 includes teeth 236 disposed around its circumference. Thread 234 of worm 207 is adapted to mate with teeth 236 of worm gear 208. Consequently, the rotation of worm 207 causes the rotation of worm gear 208.

Worm 207 and worm gear 208 collectively form a speed reducing or drive mechanism 230. In the depicted embodiment, speed reducing mechanism 230 constitutes a worm drive mechanism. It is envisioned, however, that any suitable apparatus, means, or parts, may make up speed reducing mechanism 230. For example, bevel or helical gears may form speed reducing mechanism 230. In operation, speed reducing mechanism 130 reduces the rotational speed of motor 5, while increasing torque. The present disclosure, however, also contemplates a handle assembly 12 (FIG. 1) with a drive mechanism or transmission instead of speed reducing mechanism 230. This drive mechanism transmits the rotational forces produced by motor 5 without necessarily reducing rotational speed or increasing torque.

Figure 20:
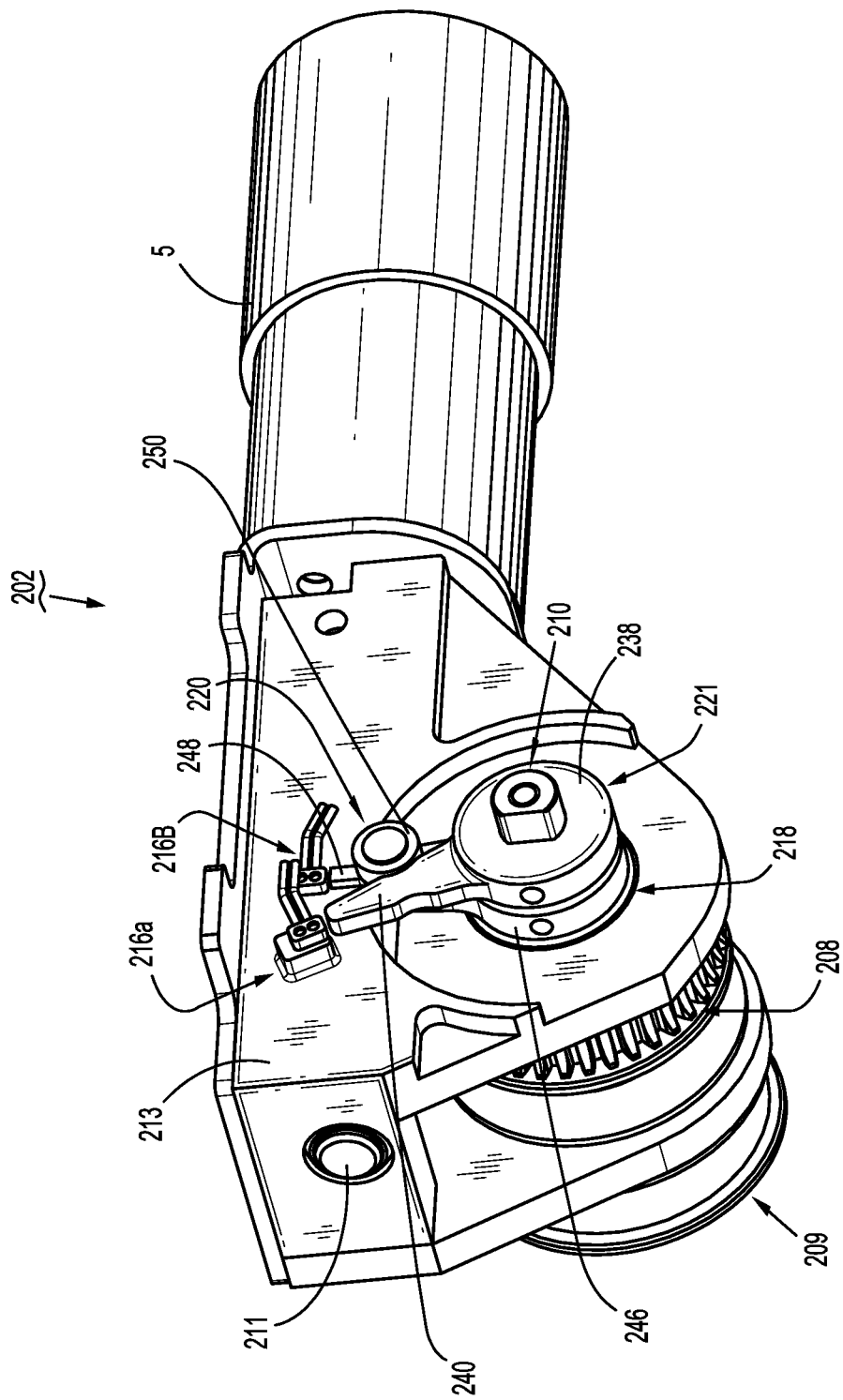
FIG. 20 is a rear perspective view of another embodiment of a retraction mechanism for use with the surgical stapling apparatus of FIG. 1.
Figure 21:
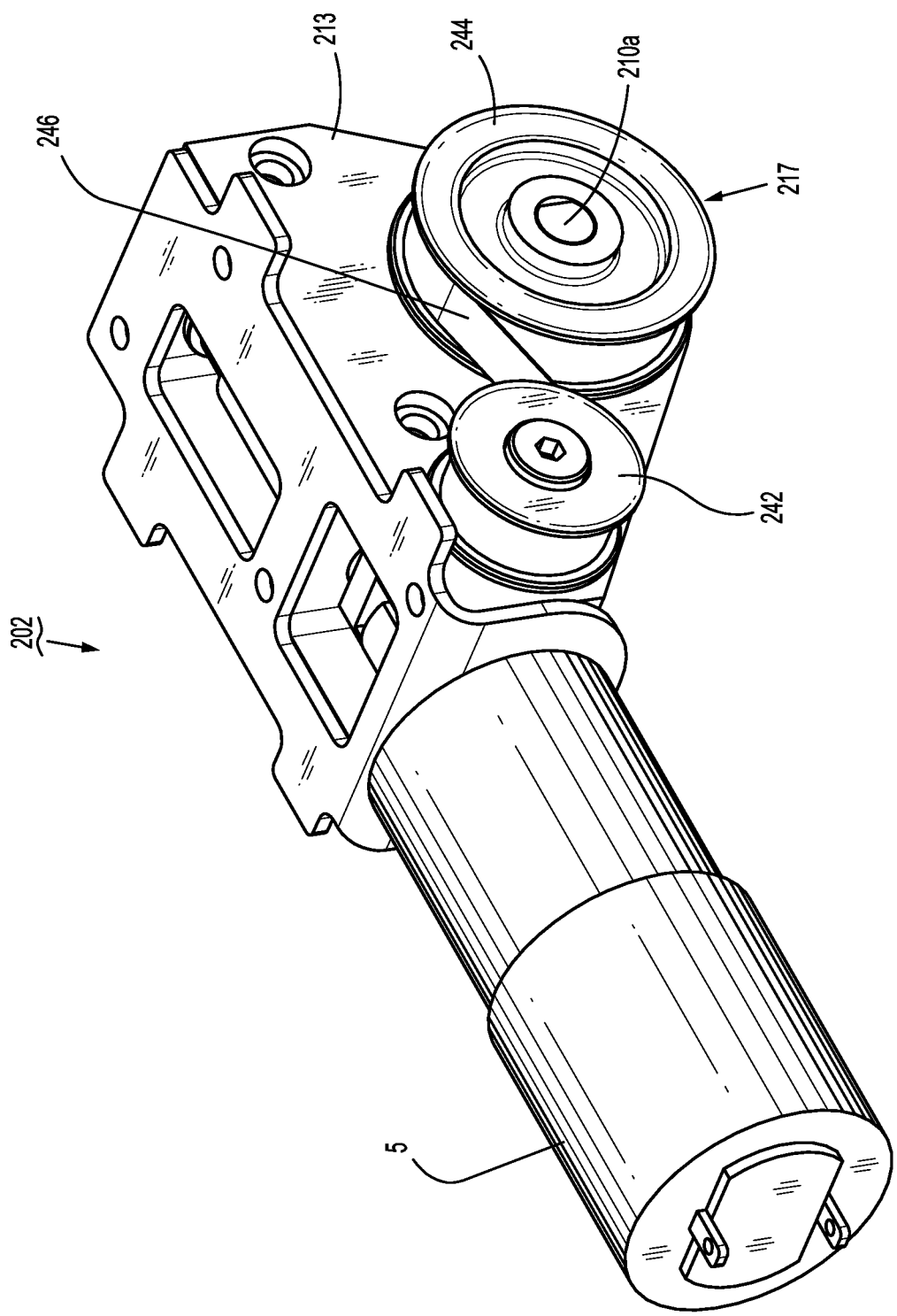
FIG. 21 is a front perspective view of the retraction mechanism of FIG. 20, showing a frame supporting certain components of the retraction mechanism.
Figure 22:
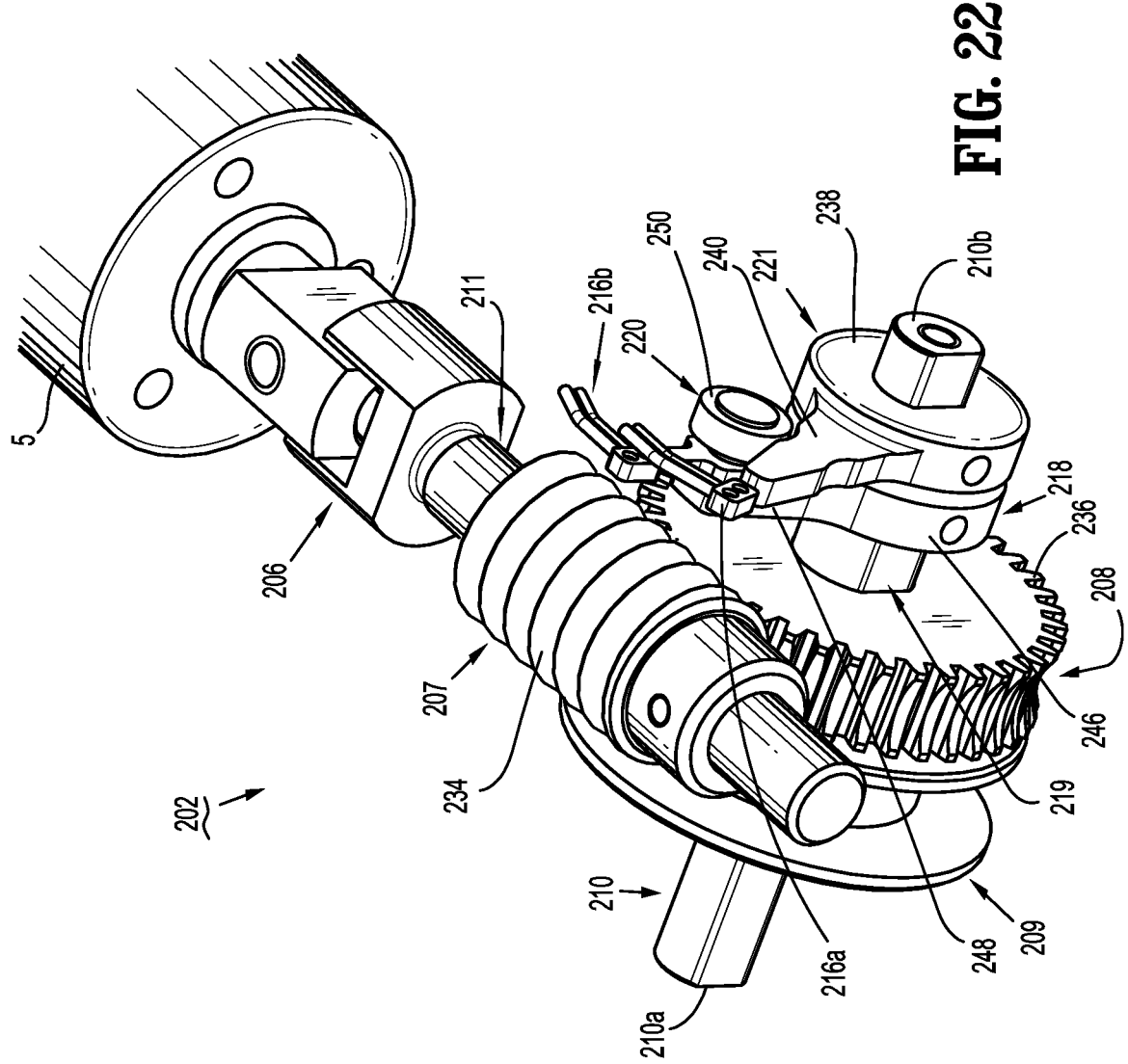
FIG. 22 is a perspective view of a proximal portion of the retraction mechanism of FIG. 20 without the frame.

In the embodiment shown in FIGS. 20-23, worm gear 208 is positioned around a shaft 210. Shaft 210 is oriented substantially orthogonal or transversely relative to shaft 211 and includes a first end 210a and a second end 210b (FIG. 22). Worm gear 208 is mounted on a hollow shaft 219. Hollow shaft 219 surrounds a portion of shaft 210 and operatively interconnects worm gear 208 and a first post 218. Worm gear 208 and first post 218 are both mounted on hollow shaft 219. As a result, worm gear 208 and arm 218 can rotate concomitantly around shaft 210 and independently of shaft 210. Specifically, first post 218 includes an annular section 246 secured to hollow shaft 218 and an arm 248 extending radially from annular section 246. An engagement member 220 is attached to arm 248 of first post 218. In the depicted embodiment, engagement member 220 has a circular cross section and is covered with a viscous and/or elastic material 250. In some embodiments, engagement member 220 is attached to arm 248 of first post 218 in a flexible manner. In any event, when subject to sudden loads, engagement member 220 is able to absorb impact energy and minimize noise. Arm 248 of first post 218 can also active first switch or sensor 216a when located in its "home" position. First sensor or switch 216a is attached to an outer wall of frame 213 (FIG. 20). It is contemplated that first sensor 216a may be a potentiometer, a Hall sensor, a piezo-electric transducer, an inductive position sensor, or any other sensor suitable to detect the position of the arm 248 of first post 218. In addition, retraction mechanism 202 may include a servomotor or a step motor to be able to constantly control the position of first post 218.

With continued reference to FIGS. 20-23, retraction mechanism 202 further includes a pulley 209 and a second post 221 both rotatably attached to shaft 210. Consequently, pulley 209 and second post 221 can rotate concomitantly with shaft 210. Pulley 209 is positioned closer to first end 210a of shaft 210 than second post 221, while second post 221 is located closer to second end 210b of shaft 210 than pulley 209. Second post 221 includes an annular section 238 mounted on shaft 210 and an arm 240 extending radially from annular section 230. Arm 240 of second post 221 can activate a second sensor or switch 216b when firing drive 2 (FIG. 4) is located in its proximal "home" position. Second sensor or switch 216b is attached to an outer wall of frame 213 (FIG. 20). It is contemplated that second sensor 216b may be a potentiometer, a Hall sensor, a piezo-electric transducer, an inductive position sensor, or any other sensor suitable to detect the position of the arm 240 of second post 221.

A flexible member 114, as described for the embodiments shown in FIGS. 15-19, interconnects firing drive 2 (FIG. 4) and pulley 209. As with previous embodiments, flexible member 114 may be a cable, a chain, a wire or any other suitable apparatus capable of connecting pulley 209 to firing drive 2. As illustrated in FIG. 21, a spring motor 217 maintains flexible member 114 in tension and prevents, or at least inhibits, its entanglement. Spring motor 217 is operatively connected to first end 210a of shaft 210 and includes a storage drum 242 attached to an outer wall of frame 213, an output drum 244 mounted for rotation on first end 210a of shaft 210, and basing member 246, such as a spring, interconnecting storage drum 242 and output drum 244.

Figure 23:
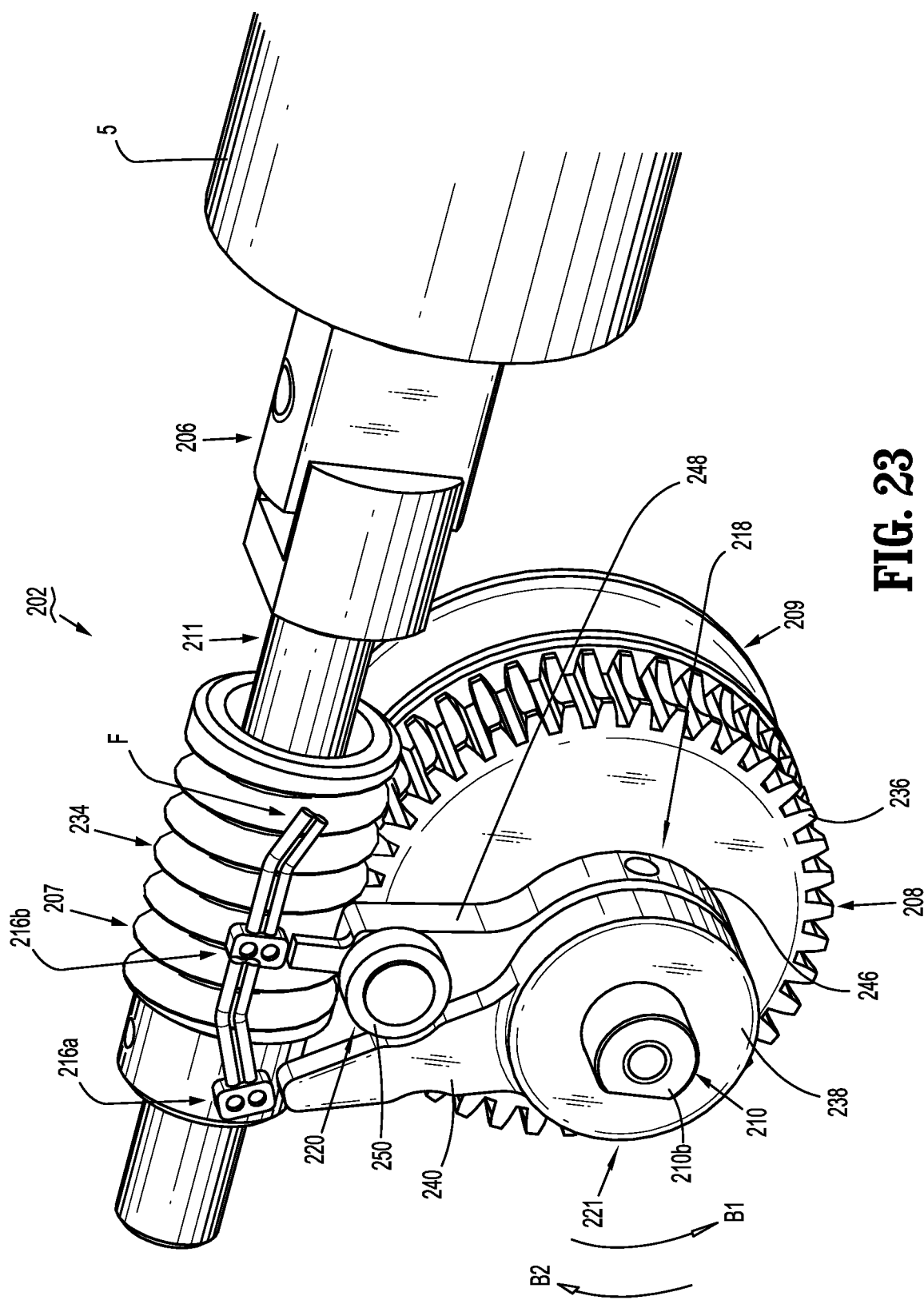
FIG. 23 is a side perspective view of the proximal portion of the retraction mechanism of FIG. 20.

In its initial state, firing drive 2 (FIGS. 4 and 19) is located at its proximal "home" position and arm 240 of second post 221 is aligned with first sensor 216a (FIG. 23). Motor 5 is turned off and, due to the friction in its gearbox, motor 5 locks shaft 211 along with worm 207. At the same time, arm 248 of first post 218 is aligned with second sensor 216b. When the operator fires surgical stapling apparatus 10 (FIG. 1), firing drive 2 moves distally. While moving distally, firing drive 2 pulls flexible member 114 (FIG. 19) in a distal direction. The distal translation of flexible member 114 causes pulley 209 to rotate in a first direction B1 (FIG. 23). Since second post 221 is connected to pulley 209 through shaft 210, second post 221 rotates in the first direction B1 when pulley 209 rotates in the first direction B1. At the end of the firing, arm 240 of second post 221 is located at position "F" (FIG. 23). The exact position "F" of arm 240 depends on the stroke applied to fire SULU 16 (FIG. 1) of a particular length.

After firing SULU 16 (FIG. 1), the operator presses a retraction switch (not shown) to turn on motor 5. Motor 5 rotates shaft 211 along with worm 207. The rotation of worm 207 causes worm gear 208 to rotate in a second direction B2 (FIG. 23). Since hollow shaft 219 rotatably couples worm gear 208 to first post 218, first post 218 rotates in the second direction B2 in response to a rotation of worm gear 208 in the second direction B2. Eventually, engagement member 220 engages arm 240 of second post 221 and urges the rotation of second post 221 together with pulley 209 in the second direction B2. While rotating in the second direction B2, pulley 209 winds flexible member 114, dragging firing drive 2 in to its proximal "home" position. Once firing drive 2 has reached its proximal "home" position, arm 240 of second post 221 is aligned with first sensor or switch 216a and consequently activates first sensor or switch 216a. Upon activation, first sensor or switch 216a sends a signal to motor 5. When the signal from first sensor or switch 216a is received, motor 5 stops and then rotates in the opposite direction to rotate worm gear 208 and first post 218 in the first direction B1 (FIG. 23). First post 218 rotates in the first direction B1 until arm 248 is aligned with second sensor or switch 216b. When arm 248 of first post 218 is aligned with second sensor or switch 216b, second sensor or switch 216b is activated. Upon activation, second sensor or switch 216b sends a signal to motor 5. Once motor 5 receives the signal from second sensor or switch 216b, motor 5 turns off and the powered retraction is completed.

Alternatively, the operator may manually retract firing drive 2 after firing surgical stapling apparatus 10 through retraction knobs 32 (FIG. 1). After firing surgical stapling apparatus 10, the operator moves retraction knobs 32 proximally along handle assembly 12 to move firing drive 2 from a distal position to a proximal "home" position. In response to this motion and due to slack in flexible member 114 (FIG. 18), spring motor 217 rotates pulley 209 and second post 221 in the second direction B2 (FIG. 23). Pulley 209 winds at least a portion of flexible member 114 (FIG. 18). At the end of the retraction, arm 240 of second post 221 is aligned with second sensor or switch 216b. At this junction, surgical stapling apparatus 10 is ready for the next cycle.

It will be understood that various modifications may be made to the embodiments disclosed herein. Therefore, the above description should not be construed as limiting, but merely exemplifications of embodiments. For instance, the described surgical stapling apparatus 10 may be used in combination with a servomotor, slide ring, electric brakes and electronic controls to add functions such as controlling retraction speed, sensing the limits with automatic stop, etc. In some embodiments, the disclosed surgical instruments include a controller, such as a microprocessor, which can control different parameters of the motors, such as motor travel, speed and direction of rotation based on input from the sensors and/or activation switches. In addition, the disclosed retraction mechanisms may be incorporated to other surgical instruments such as clip appliers. Those skilled in the art will envision other modification within the scope and spirit of the claims appended thereto.

What it is claimed is:

1. A retraction mechanism for use with a surgical apparatus comprising:
   a first shaft configured to rotate about a first axis;
   a pulley configured to rotate about the first axis;
   a first post operatively coupled to the first shaft, wherein the first post is configured to rotate about the first axis upon rotation of the first shaft;
   a second post operatively connected to the pulley, wherein the second post is configured to rotate concomitantly with the pulley about the first axis; and
   an engagement member operatively engaged with the first post and configured to engage the second post, wherein the second post is configured to rotate concomitantly with the first post when the engagement member engages the second post.

2. The retraction mechanism according to claim 1, further including a motor configured to drive a motor shaft about a second axis, the motor shaft disposed in mechanical cooperation with the first shaft.

3. The retraction mechanism according to claim 2, further including a first sensor configured to be activated by the first post.

4. The retraction mechanism according to claim 3, wherein the first sensor is electrically coupled to the motor.

5. The retraction mechanism according to claim 4, wherein the motor is configured to stop upon activation of the first sensor by the first post.

6. The retraction mechanism according to claim 3, further including a second sensor configured to be activated by the second post, the second sensor being electrically coupled to the motor.

7. The retraction mechanism according to claim 6, wherein the motor is configured to rotate in a first direction prior to activation of the first sensor, the motor is configured to stop rotating upon activation of the first sensor, and the motor is configured to rotate in a second direction upon activation of the second sensor, the second direction being opposite from the first direction.

8. The retraction mechanism according to claim 1, further including a speed reducing mechanism disposed in mechanical cooperation with the motor shaft.

9. The retraction mechanism according to claim 8, wherein the speed reducing mechanism includes a worm secured to the motor shaft.

10. The retraction mechanism according to claim 9, wherein the speed reducing mechanism includes a worm gear configured to mate with the worm.

11. The retraction mechanism according to claim 10, further including a hollow shaft interconnecting the worm gear and the first post.

12. The retraction mechanism according to claim 11, further including a second shaft interconnecting the pulley and the second post.

13. The retraction mechanism according to claim 12, wherein at least a portion of the second shaft is positioned inside of the hollow shaft.

14. The retraction mechanism according to claim 1, wherein rotation of the pulley about the first axis is configured to move a firing drive of the surgical apparatus proximally.

15. The retraction mechanism according to claim 1, wherein the engagement member attached to the first post.

16. A retraction mechanism for use with a surgical apparatus comprising:
- a motor shaft configured to rotate about a first axis;
- a first post operatively coupled to the motor shaft, wherein the first post is configured to rotate about a second axis upon rotation of the motor shaft, the second axis being perpendicular to the first axis;
- an arm extending from the first post and configured to rotate about the second axis upon rotation of the motor shaft;
- a sensor configured for selective engagement by the arm;
- a second post disposed in mechanical cooperation with the first post; and
- an engagement member operatively engaged with the arm and configured to engage the second post, wherein the second post is configured to rotate concomitantly with the first post when the engagement member engages the second post.

17. The retraction mechanism according to claim 16, further including a pulley configured to rotate about the second axis and operatively connected to the second post.

18. The retraction mechanism according to claim 16, further including a motor configured to drive the motor shaft.

19. The retraction mechanism according to claim 16, further including a speed reducing mechanism disposed in mechanical cooperation with the motor shaft.

20. The retraction mechanism according to claim 19, wherein the speed reducing mechanism includes a worm secured to the motor shaft and a worm gear configured to mate with the worm.

* * * * *